(12) United States Patent
Blott et al.

(10) Patent No.: US 7,794,450 B2
(45) Date of Patent: Sep. 14, 2010

(54) WOUND CLEANSING APPARATUS WITH HEAT

(75) Inventors: Patrick Lewis Blott, Barmby Moor (GB); Bryan Greener, Elvington (GB); Edward Yerbury Hartwell, Hull (GB); Julian Lee-Webb, Copmanthorpe (GB); Derek Nicolini, Brough (GB); Clare Green, Crockey Hill (GB); Robin Paul Martin, Wheldrake (GB)

(73) Assignee: Smith & Nephew PLC, London (GB)

( * ) Notice: Subject to any disclaimer, the term of this patent is extended or adjusted under 35 U.S.C. 154(b) by 92 days.

(21) Appl. No.: 10/575,875

(22) PCT Filed: Oct. 28, 2004

(86) PCT No.: PCT/GB2004/004564

§ 371 (c)(1),
(2), (4) Date: Feb. 1, 2007

(87) PCT Pub. No.: WO2005/046760

PCT Pub. Date: May 26, 2005

(65) Prior Publication Data

US 2007/0129707 A1 Jun. 7, 2007

(30) Foreign Application Priority Data

Oct. 28, 2003 (GB) ................................. 0325126.1

(51) Int. Cl.
*A61M 27/00* (2006.01)
(52) U.S. Cl. ........................ 604/543; 604/319; 604/320; 604/321; 604/322; 604/323; 604/305; 604/306; 604/307; 604/308; 128/897; 128/898; 602/42; 602/43; 602/44; 602/45; 602/46; 602/47; 602/48; 602/49; 602/50; 602/51; 602/52; 602/53

(58) Field of Classification Search ......... 604/319–323, 604/305–308
See application file for complete search history.

(56) References Cited

U.S. PATENT DOCUMENTS 2,280,915 A    4/1941 Johnson (Continued)

FOREIGN PATENT DOCUMENTS

CA    2 369 022    10/2001

(Continued)

OTHER PUBLICATIONS

U.S. Appl. No. 10/599,722, filed Oct. 6, 2006, Blott et al.

(Continued)

*Primary Examiner*—Tatyana Zalukaeva
*Assistant Examiner*—Ilya Y Treyger
(74) *Attorney, Agent, or Firm*—Knobbe Martens Olson & Bear LLP

(57) ABSTRACT

An apparatus for cleansing and promoting tissue growth in wounds, in which irrigant fluid optionally containing cell nutrients and/or other physiologically active material from a reservoir connected to a conformable wound dressing and wound exudate from the dressing are recirculated by a device for moving fluid through a flow path which passes through the dressing, a biodegradable scaffold in contact with the wound bed and a means for fluid cleansing and back to the dressing. The apparatus has means for supplying thermal energy to the fluid in the wound. The cleansing means (which may be a single-phase, e.g. micro-filtration, system or a two-phase, e.g. dialytic system) removes materials deleterious to wound healing, and the cleansed fluid, still containing materials that are beneficial in promoting wound healing, is returned to the wound bed. The dressing and a method of treatment using the apparatus.

23 Claims, 8 Drawing Sheets

U.S. PATENT DOCUMENTS

| | | | |
|---|---|---|---|
| 3,874,387 A | 4/1975 | Barbieri | |
| 3,993,080 A | 11/1976 | Loseff | |
| 4,112,947 A | 9/1978 | Nehring | |
| 4,136,696 A | 1/1979 | Nehring | |
| 4,184,510 A | 1/1980 | Murry et al. | |
| 4,224,945 A | 9/1980 | Cohen | |
| 4,316,466 A | 2/1982 | Babb | |
| 4,382,441 A | 5/1983 | Svedman | |
| 4,465,485 A | 8/1984 | Kashmer et al. | |
| 4,540,412 A | 9/1985 | Van Overloop | |
| 4,573,965 A | 3/1986 | Russo | |
| 4,778,446 A | 10/1988 | Jensen | |
| 4,792,328 A | 12/1988 | Beck et al. | |
| 4,921,488 A | 5/1990 | Maitz et al. | |
| 4,936,834 A | 6/1990 | Beck et al. | |
| 4,969,880 A | 11/1990 | Zamierowski | |
| 4,979,944 A * | 12/1990 | Luzsicza | 604/118 |
| 5,009,635 A * | 4/1991 | Scarberry | 604/27 |
| 5,055,198 A * | 10/1991 | Shettigar | 210/650 |
| 5,073,172 A | 12/1991 | Fell | |
| 5,100,396 A | 3/1992 | Zamierowski | |
| 5,176,663 A | 1/1993 | Svedman et al. | |
| 5,261,893 A | 11/1993 | Zamierowski | |
| 5,328,614 A | 7/1994 | Matsumura | |
| 5,358,494 A | 10/1994 | Svedman | |
| 5,380,280 A | 1/1995 | Peterson | |
| 5,498,338 A | 3/1996 | Kruger et al. | |
| 5,549,584 A | 8/1996 | Gross | |
| 5,636,643 A * | 6/1997 | Argenta et al. | 128/897 |
| 5,645,081 A | 7/1997 | Argenta et al. | |
| 5,759,570 A | 6/1998 | Arnold | |
| 5,954,680 A * | 9/1999 | Augustine | 602/42 |
| 6,110,197 A | 8/2000 | Augustine et al. | |
| 6,254,567 B1 | 7/2001 | Treu et al. | |
| 6,398,767 B1 | 6/2002 | Fleischmann | |
| 6,458,109 B1 | 10/2002 | Henley et al. | |
| 6,465,708 B1 | 10/2002 | Augustine | |
| 6,520,982 B1 | 2/2003 | Boynton et al. | |
| 6,626,827 B1 | 9/2003 | Felix et al. | |
| 6,685,681 B2 | 2/2004 | Lockwood et al. | |
| 6,695,824 B2 | 2/2004 | Howard et al. | |
| 6,752,794 B2 | 6/2004 | Lockwood et al. | |
| 6,755,807 B2 | 6/2004 | Risk et al. | |
| 6,800,074 B2 * | 10/2004 | Henley et al. | 604/319 |
| 7,077,832 B2 | 7/2006 | Fleischmann | |
| 7,108,683 B2 | 9/2006 | Zamierowski | |
| 7,144,390 B1 | 12/2006 | Hannigan et al. | |
| 7,195,624 B2 | 3/2007 | Lockwood | |
| 7,216,651 B2 | 5/2007 | Argenta et al. | |
| 7,361,184 B2 | 4/2008 | Joshi | |
| 7,494,482 B2 | 2/2009 | Orgill et al. | |
| 7,524,315 B2 | 4/2009 | Blott et al. | |
| 7,534,927 B2 | 5/2009 | Lockwood et al. | |
| 7,540,848 B2 | 6/2009 | Hannigan et al. | |
| 2001/0034499 A1 | 10/2001 | Sessions et al. | |
| 2002/0161346 A1 | 10/2002 | Lockwood et al. | |
| 2003/0021775 A1 | 1/2003 | Freeman | |
| 2003/0050594 A1 | 3/2003 | Zamierowski | |
| 2003/0108587 A1 | 6/2003 | Orgill et al. | |
| 2003/0144619 A1 | 7/2003 | Augustine | |
| 2003/0171675 A1 | 9/2003 | Rosenberg | |
| 2004/0054338 A1 | 3/2004 | Bybordi et al. | |
| 2006/0155260 A1 | 7/2006 | Blott | |
| 2007/0038172 A1 | 2/2007 | Zamierowski | |
| 2007/0066945 A1 * | 3/2007 | Martin | 604/313 |
| 2007/0073200 A1 | 3/2007 | Hannigan et al. | |
| 2007/0141128 A1 * | 6/2007 | Blott et al. | 424/445 |
| 2007/0167926 A1 * | 7/2007 | Blott et al. | 604/304 |
| 2007/0293830 A1 * | 12/2007 | Martin | 604/289 |
| 2008/0294127 A1 * | 11/2008 | Blott et al. | 604/305 |
| 2009/0012483 A1 * | 1/2009 | Blott et al. | 604/315 |
| 2009/0054855 A1 * | 2/2009 | Blott et al. | 604/290 |
| 2009/0069759 A1 * | 3/2009 | Blott et al. | 604/290 |
| 2009/0143753 A1 * | 6/2009 | Blott et al. | 604/315 |
| 2009/0204084 A1 * | 8/2009 | Blott et al. | 604/290 |
| 2009/0221977 A1 * | 9/2009 | Blott et al. | 604/290 |
| 2009/0234260 A1 | 9/2009 | Coward et al. | |

FOREIGN PATENT DOCUMENTS

| | | |
|---|---|---|
| DE | 3935818 A1 | 5/1991 |
| DE | 40 12 232 | 10/1991 |
| DE | 198 44 355 | 4/2000 |
| EP | 0020662 B1 | 7/1984 |
| EP | 0 777 504 B1 | 8/1995 |
| EP | 0 853 950 B1 | 8/1995 |
| EP | 0 880 953 B1 | 5/1998 |
| FR | 1 163 907 | 10/1958 |
| GB | 114754 | 4/1918 |
| GB | 641061 | 8/1950 |
| GB | 1 224 009 A | 3/1971 |
| GB | 1549756 A | 8/1979 |
| GB | 2195255 A | 4/1988 |
| GB | 2378392 A | 2/2003 |
| SU | 1251912 A1 | 4/1983 |
| WO | WO 84/01904 | 5/1984 |
| WO | WO84/01904 * | 5/1984 |
| WO | WO 84/19044 | 5/1984 |
| WO | WO 90/11795 | 10/1990 |
| WO | WO 91/00718 | 1/1991 |
| WO | WO 92/19313 | 11/1992 |
| WO | WO 92/20299 | 11/1992 |
| WO | WO 00/07653 | 2/2000 |
| WO | WO 00/50143 | 8/2000 |
| WO | WO00/50143 * | 8/2000 |
| WO | WO 02/083046 A1 | 10/2002 |
| WO | WO 02/092783 | 11/2002 |
| WO | WO 2004/037334 | 5/2004 |
| WO | WO 2007/019038 | 2/2007 |
| WO | WO 2008/010094 | 1/2008 |

OTHER PUBLICATIONS

U.S. Appl. No. 10/599,725, filed Oct. 6, 2006, Blott et al.
U.S. Appl. No. 10/599,728, filed Oct. 6, 2006, Blott et al.
U.S. Appl. No. 11/919,354, filed Oct. 26, 2007, Blott et al.
U.S. Appl. No. 11/919,355, filed Oct. 26, 2007, Blott et al.
U.S. Appl. No. 11/919,369, filed Oct. 26, 2007, Blott et al.
U.S. Appl. No. 11/957,860, filed Dec. 17, 2007, Blott et al.
U.S. Appl. No. 12/066,578, filed Mar. 12, 2008, Blott et al.
U.S. Appl. No. 12/066,585, filed Mar. 12, 2008, Blott et al.
U.S. Appl. No. 12/066,730, filed Mar. 13, 2008, Blott et al.
U.S. Appl. No. 12/094,963, filed May 23, 2008, Dagger.
Aubrey, D.A., et al., Treatment of the Perineal Wound after Proctectomy by Intermittent Irrigation, Arch. Surg., Oct. 1984, vol. 119, pp. 1141-1144.
Chariker, M.E., et al, Effective Management of Incisional and Cutaneous Fistulae with Closed Suction Wound Drainage, Contemporary Surgery. Jun. 1989, vol. 34 USA, pp. 59-63.
Dilmaghani et al., A Method for Closed Irrigation and Suction Therapy in Deep Wound Infections, Journal of Bone and Joint Surgery, 1969, vol. 51-A, No. 2, pp. 323-342.
Hartz, R.S., et al., Healing of the Perineal Wound, Arch. Surg., Apr. 1980, vol. 115, pp. 471-474.
International Preliminary Patent Report for International Application No. PCT/GB2004/004564, date of report issuance Dec. 13, 2005 in 8 pages.
International Search Report for International Application No. PCT/GB2004/004564, date of mailing Feb. 23, 2005 in 4 pages.
Nursing75, "Wound Suction", Nursing, USA, pp. 52-53.

Svedman, P., Irrigation Treatment in Split-Thickness Skin Grafting of Intractable Leg Ulcers, Scand J. Plast. Reconst. Surg., 1985, vol. 19, pp. 211-213.
Svedman, P., Irrigation Treatment of Leg Ulcers, The Lancet, Sep. 1983, pp. 532-534.
Svedman, P., A Dressing Allowing Continuous Treatment of a Biosurface, IRCS Med. Science: Biomed. Tech.; Clinic. Med.; Surg. and Transplantation, 1979, vol. 7, p. 221.
Svedman, P., et al., A Dressing System Providing Fluid Supply and Suction Drainage Used for Continuous or Intermittent irrigation, Annals of Plastic Surgery, vol. 17, No. 2, Aug. 1986, pp. 125-133.
Swift, et al, Quorum Sensing in *Aeromonas hydrophila* and *Aeromonas salmoncida*: Identification of LuxRl Homologs AhyRl and AsaRl and Their Cognate N-Acylhomoserine Lactone Signal Molecules, J. Bacteriol., 1997, vol. 179, No. 17, pp. 5271-5281.
Teder and Svedman et al., Continuous Wound Irrigation in the Pig, Journal of Investigative Surgery, 1990, vol. 3, pp. 399-407.
Tribble, David E. M.D., An Improved Sump Drain-Irrigation Device of Simple Construction, Archives of Surgery New York, 1972, vol. 105, pp. 511-513.
Vijanto, J. and J. Raekallio, Local Hyperalimentation of Open Wounds, Br. J. surg., 1976, vol. 63, pp. 427-430.
Westaby, S., et al., A Wound Irrigation Device, The Lancet, Sep. 2, 1978, pp. 503-504.
Wooding-Scott, Margaret, et al., No Wound is Too Big for Resourceful Nurses, RN, USA, Dec. 1988, pp. 22-25.
U.S. Appl. No. 12/416,829, filed Apr. 1, 2009, and its ongoing prosecution history, including without limitation Office Actions, Amendments, Remarks, and any other potentially relevant documents, Dagger.
U.S. Appl. No. 10/576,263, filed Nov. 9, 2006, published as 2007/0141128, and its ongoing prosecution history, including without limitation Office Actions, Amendments, Remarks, and any other potentially relevant documents, Jun. 21, 2007, Blott et al.
U.S. Appl. No. 10/575,871, filed Jan. 29, 2007, published as 2007/0167926, and its ongoing prosecution history, including without limitation Office Actions, Amendments, Remarks, and any other potentially relevant documents, Jul. 19, 2007, Blott et al.
U.S. Appl. No. 10/575,870, filed Apr. 17, 2006, published as 2007/0066945, and its ongoing prosecution history, including without limitation Office Actions, Amendments, Remarks, and any other potentially relevant documents, Mar. 22, 2007, Martin.
U.S. Appl. No. 11/957,860, filed Dec. 12, 2007, published as 2008/0294127, and its ongoing prosecution history, including without limitation Office Actions, Amendments, Remarks, and any other potentially relevant documents, Nov. 27, 2008, Blott et al.
U.S. Appl. No. 10/599,722, filed Sep. 19, 2008, published as 2009/0012483, and its ongoing prosecution history, including without limitation Office Actions, Amendments, Remarks, and any other potentially relevant documents, Jan. 8, 2009, Blott et al.
U.S. Appl. No. 10/599,725, filed Sep. 22, 2008, published as 2009/0069759, and its ongoing prosecution history, including without limitation Office Actions, Amendments, Remarks, and any other potentially relevant documents, Mar. 12, 2009, Blott et al.
U.S. Appl. No. 10/599,728, filed Nov. 3, 2008, published as 2009/0054855, and its ongoing prosecution history, including without limitation Office Actions, Amendments, Remarks, and any other potentially relevant documents, Feb. 26, 2009, Blott et al.
U.S. Appl. No. 11/577,642, filed Aug. 23, 2007, published as 2007/0293830, and its ongoing prosecution history, including without limitation Office Actions, Amendments, Remarks, and any other potentially relevant documents, Dec. 20, 2007, Martin.
U.S. Appl. No. 11/919,355, filed Oct. 26, 2007, and its ongoing prosecution history, including without limitation Office Actions, Amendments, Remarks, and any other potentially relevant documents, Blott et al.
U.S. Appl. No. 11/919,369, filed Oct. 26, 2007, and its ongoing prosecution history, including without limitation Office Actions, Amendments, Remarks, and any other potentially relevant documents, Blott et al.
U.S. Appl. No. 11/919,354, filed Oct. 26, 2007, and its ongoing prosecution history, including without limitation Office Actions, Amendments, Remarks, and any other potentially relevant documents, Blott et al.
U.S. Appl. No. 12/066,578, filed Oct. 10, 2008, and its ongoing prosecution history, including without limitation Office Actions, Amendments, Remarks, and any other potentially relevant documents, Blott et al.
U.S. Appl. No. 12/066,730, filed Oct. 9, 2008, published as 2009/0143753, and its ongoing prosecution history, including without limitation Office Actions, Amendments, Remarks, and any other potentially relevant documents, Jun. 4, 2009, Blott et al.
U.S. Appl. No. 12/066,585, filed Sep. 29, 2008, and its ongoing prosecution history, including without limitation Office Actions, Amendments, Remarks, and any other potentially relevant documents, Blott et al.
U.S. Appl. No. 12/300,636, filed Nov. 12, 2008, and its ongoing prosecution history, including without limitation Office Actions, Amendments, Remarks, and any other potentially relevant documents, Fry et al.
U.S. Appl. No. 10/652,100, filed Aug. 28, 2003, published as 2004/0073151, and its ongoing prosecution history, including without limitation Office Actions, Amendments, Remarks, and any other potentially relevant documents, Weston.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English Translation).
Examinarion Report for International Application No. PCT/GB2004/004564, date of mailing Jun. 11, 2008 in 3 pages.
Reply to Examination Report, dated Jun. 11, 2008 for International Application No. PCT/GB2004/004564, date of mailing Dec. 11, 2008 in 7 pages.

* cited by examiner

Section View on X-X

WOUND CLEANSING APPARATUS WITH HEAT

The present invention relates to apparatus and a medical wound dressing for irrigating, supplying thermal energy to and cleansing wounds, and a method of treating wounds using such apparatus for irrigating, supplying thermal energy to and cleansing wounds.

It relates in particular to such an apparatus, wound dressing and method that can be easily applied to a wide variety of, but in particular chronic, wounds, to cleanse them of materials that are deleterious to wound healing, whilst retaining materials that are beneficial in some therapeutic aspect, in particular to wound healing.

Before the present invention, aspirating and/or irrigating wounds and apparatus therefor were known, and tended to be used to remove wound exudate during wound therapy. In known forms of such wound therapy, the offtake from the wound, especially when in a highly exuding state, is voided to waste, e.g. to a collection bag.

Materials deleterious to wound healing are removed in this way.

However, materials that are beneficial in promoting wound healing, such as growth factors, naturally occurring anti-inflammatories, and other physiologically active components of the exudate from a wound are lost to the site where they can be potentially of most benefit, i.e. the wound bed, when such therapy is applied.

It thus would be desirable to provide a system of therapy which a) can remove materials deleterious to wound healing from wound exudate, whilst retaining materials that are beneficial in promoting wound healing in contact with the wound bed, and/or b) which allows fluids containing active amounts of materials that are beneficial in promoting wound healing to pass into and/or through the wound in contact with the wound bed.

Dialysis is a known method of treating bodily fluids such as blood ex vivo, to cleanse them of materials that are deleterious to the body systemically. Retaining materials that are beneficial in some therapeutic aspect in the treated fluid is not an object of dialysis.

This method of treating bodily fluids is also a systemic therapy, since the treated fluid is returned to within the body. This is in contrast to a topical therapy in which the treated fluid is recycled outside the body, e.g. to a wound.

Dialysis also requires large amounts either of bodily fluids, such as blood, or of dialysate, and consequently the relevant devices tend not to be portable.

Even when in a highly exuding state, chronic wounds produce relatively little fluid to be treated and relatively little materials that are beneficial in some therapeutic aspect to be retained in the wound and/or its environment.

It is an object of the present invention a) to obviate at least some of the abovementioned disadvantages of known aspiration and/or irrigation therapy systems, and b) to provide a system of therapy which can remove materials deleterious to wound healing from wound exudate, whilst retaining materials that are beneficial in promoting wound healing in contact with the wound bed, It is a further object of the present invention a) to obviate at least some of the abovementioned disadvantages of known dialysis systems, and b) to provide a system of therapy which can remove materials deleterious to wound healing from wound exudate, whilst retaining materials that are beneficial in promoting wound healing in contact with the wound bed, c) without affecting the body systemically.

It is a yet further object of the present invention a) to obviate at least some of the abovementioned disadvantages of known dialysis systems, and b) to provide a system of therapy which can remove materials deleterious to wound healing from wound exudate, whilst retaining materials that are beneficial in promoting wound healing in contact with the wound bed, c) without affecting the body systemically, and d) which is portable.

Additionally, it is generally believed that the body's own metabolic activities are at an optimum at or near the temperature naturally occurring in the relevant bodily part.

Examples of metabolic molecules involved in tissue healing processes that are beneficial in promoting wound healing include enzymes, growth factors and anti-inflammatories, and other physiologically active components of the exudate from a wound.

These are believed to act best at temperatures found in the relevant bodily part in which they occur, varying between normal temperatures found at the body surface and those at the body core.

The body core is at a higher temperature than the surface, but surface temperatures at 33° C. and above are still relatively close to core body temperatures of 36 to 38° C. ('normothermic temperature'). Wounds, and in particular chronic wounds, may have a lower temperature, e.g. 24 to 26° C., i.e. substantially below the optimum temperature. Thus, the temperature of the wound itself is deleterious to wound healing.

This may result in slow wound healing, loss of cell proliferation, and/or growth that does not have a strong three-dimensional structure adhering well to and growing from the wound bed.

Conventional wound aspiration and/or irrigation therapy systems thus often create a wound environment under a backing layer where a) not only are beneficial materials lost to the site where they can be potentially of most benefit, i.e. the wound bed, when such therapy is applied, but b) the wound healing processes, e.g. enzymic activity on tissue growth, are inhibited by sub-optimal temperatures.

Heated dressings are known, but such forms of wound dressing do not simultaneously irrigate the wound environment under the backing layer.

This will result in materials deleterious to wound healing in wound exudate being retained in the wound environment and hindering wound healing in spite of any stimulation of wound healing from wound temperature regulation.

There would thus be an advantage, in particular in chronic wounds, in providing means for more than one therapy in a single dressing.

a) which not only removes materials deleterious to wound healing from wound exudate, whilst retaining materials that are beneficial in promoting wound healing in contact with the wound bed, but b) promotes wound healing by creating a wound environment under the dressing with temperatures which stimulate the activity of metabolic molecules that are beneficial in promoting wound healing, e.g. temperatures near 36 to 38° C. ('normothermic temperature').

It is an object of the present invention a) to obviate at least some of the abovementioned disadvantages of known wound dressing, and b) to provide a system of therapy which cleanses wounds, but also supplies thermal energy to the wound. in particular one which
   i) can remove materials deleterious to wound healing from wound exudate, whilst retaining materials that are beneficial in promoting wound healing in contact with the wound bed, and
   ii) maintains wounds at or near normothermic temperature,
It is an object of the present invention
a) to obviate at least some of the abovementioned disadvantages of known wound dressing, and
b) to provide a system of therapy that conveniently cleanses wounds, but also maintains wounds at or near normothermic temperature.

A disadvantage of known heated wound dressings is that it is imperative but not easy to avoid the heater, especially an electrical heater, from scorching the wound and/or surrounding surfaces. This is especially so when the dressing is in contact with the wound bed.

Several devices for applying to the wound to try to do so have been proposed. In one form, a stiff flange or lip extends around the periphery of the dressing to space the surface of the wound in use away from the heater. Such a wound dressing is cumbersome. Whilst it may be acceptable for hospital use, the stiff flange does little for patient comfort, and heightens the risk of inflammation of a wound and/or the leakage of wound exudate. There would be a further advantage in providing such a wound dressing that conforms to the shape of the bodily part to which it is applied.

It is an object of the present invention
a) to obviate at least some of the abovementioned disadvantages of known wound dressing, and
b) to provide a system of therapy which
   i) can remove materials deleterious to wound healing from wound exudate, whilst retaining materials that are beneficial in promoting wound healing in contact with the wound bed,
   ii) which supplies thermal energy to and/or through the wound, and
   iii) comprises a conformable wound dressing.

Thus, according to a first aspect of the present invention there is provided an apparatus for irrigating, supplying thermal energy to, and cleansing wounds, characterised in that it comprises
a) a fluid flow path, comprising
   i) a conformable wound dressing, having
      a backing layer which is capable of forming a relatively fluid-tight seal or closure over a wound and
      at least one inlet pipe for connection to a fluid supply tube, which passes through and/or under the wound-facing face, and
      and at least one outlet pipe for connection to a fluid offtake tube, which passes through and/or under the wound-facing face,
      the point at which the or each inlet pipe and the or each outlet pipe passes through and/or under the wound-facing face forming a relatively fluid-tight seal or closure over the wound,
      at least one inlet pipe being connected to a fluid recirculation tube, and at least one outlet pipe being connected to a fluid offtake tube: and
   ii) a means for fluid cleansing having at least one inlet port connected to a fluid offtake tube and at least one outlet port connected to a fluid recirculation tube;
b) a fluid reservoir connected by a fluid supply tube to an integer of the flow path (optionally or as necessary via means for flow switching between supply and recirculation);
c) a device for moving fluid through the wound dressing and means for fluid cleansing, and optionally or as necessary the fluid supply tube;
d) the apparatus having means for supplying thermal energy to the fluid in the wound,
and
e) optionally means for bleeding the flowpath, such that fluid may be supplied to fill the flowpath from the fluid reservoir via the fluid supply tube (optionally or as necessary via the means for flow switching) and recirculated by the device through the flow path.

Where any pipe is described in connection with the operation of the apparatus as being connected or for connection to a (mating end of a) tube, e.g. a fluid supply tube, fluid recirculation tube or fluid offtake tube, the pipe and the tube may form a single integer in the flow path through which the circulating fluid from the wound passes.

An advantage of such wound dressings is that it is easy to avoid overheating of the wound and/or surrounding surfaces, especially by electrical heating, since the heating must always pass to the wound through a heat transfer medium (the irrigant). This eliminates direct contact of the wound bed with the heater, and irrigant may be used as a heat transfer medium in a highly controllable manner.

The apparatus is most favourable to the wound healing process in chronic wounds, and thus for irrigating, supplying thermal energy to, and cleansing wounds such as diabetic foot ulcers, and especially decubitus pressure ulcers.

However, thermal energy may also appropriately be applied using the apparatus to aid the healing process in other wound types, such as acute and/or surgical wounds, including burns.

In a preferred mode, the present invention is used to provide a system of therapy which conveniently cleanses wounds, but also maintains them at or near normothermic temperature.

Accordingly a preferred type of the apparatus of the invention for irrigating, supplying thermal energy to and cleansing wounds is provided with means for maintaining the wound at or near normothermic temperatures.

As noted above, the apparatus of the present invention for irrigating, supplying thermal energy to, and cleansing wounds has a direct effect on active components of fluid in contact with the wound, in particular solutes or disperse phase species that are beneficial in promoting wound healing that are in contact with the wound bed. Additionally, cell mitochondria aid proliferation and hence wound healing, in particular in chronic wounds, and are stimulated by near infrared radiation.

Application of such radiation to the wound resulting in an increase in cell proliferation in the tissue underlying to the wound, and in the breaking strength of the new tissue.

Other physiologically active components of the cells in the tissue underlying the wound that are beneficial in promoting wound healing may also be stimulated by radiation on the wound.

Examples of means for supplying thermal energy to the fluid in the wound include as may be appropriate conducted thermal energy, electromagnetic radiation of an appropriate wavelength, or (less often) as convected thermal energy.

In the present apparatus, heat will usually be conducted to the wound bed by the irrigant and/or wound exudate within the dressing.

However, thermal energy may as appropriate be supplied to the irrigant and/or wound exudate within the dressing, and may be applied to the fluid by any suitable means, at any suitable point, often depending on particular components and/or materials that are used.

Examples of such means include a) direct conductive contact of the irrigant and/or wound exudate with a heater and/or conductively heated component of the apparatus flow path;
b) direct electromagnetic irradiation at an appropriate wavelength, e.g. infrared and/or near infrared from a radiative heater of the irrigant fluid and/or wound exudate; and/or
c) electromagnetic irradiation from a radiative heater of a component of the apparatus flow path that absorbs electromagnetic irradiation at an appropriate wavelength, e.g. infrared and/or near infrared and is in direct conductive contact with the irrigant and/or wound exudate.

Accordingly, one embodiment of the present apparatus for irrigating, supplying thermal energy to and cleansing wounds supplying thermal energy to and cleansing wounds is characterised in that it comprises means for providing thermal energy to the fluid in the wound.

Another embodiment of the present apparatus for irrigating, supplying thermal energy to and cleansing wounds is characterised in that it comprises means for supplying electromagnetic radiation of an appropriate wavelength to the fluid in the wound.

Another embodiment of the present apparatus for irrigating, supplying thermal energy to and cleansing wounds is characterised in that it comprises means for supplying electromagnetic radiation of an appropriate wavelength to the fluid in the wound.

The heater of the irrigant fluid and/or wound exudate and/or heated component of the apparatus flow path may be at any convenient or appropriate position or component of the apparatus flow path.

Examples include a heater and/or conductively heated component of the apparatus flow path a) mounted distally of the body on, in or inside of the dressing;
b) mounted in, on, at or near one or more of the fluid inlet pipe(s) and outlet pipe(s) that pass through and/or under the wound-facing face of the backing layer;
c) mounted in, on, at or near one or more of the connectors in the tubes that form the flow path of the apparatus;
d) mounted in, on, at or near the reservoir; and/or
e) mounted in, on, at or near the means for fluid cleansing.

As noted above, the irrigant and/or wound exudate fluid in the interior of the wound dressing is beneficially maintained at a temperature that is at or near the temperature naturally occurring in the relevant bodily part and/or normothermic temperature.

The desired or optimum temperature of the wound will substantially determine a) the position along the apparatus flow path or the component of the apparatus flow path where the heater and/or conductively heated component of the apparatus flow path is mounted relative to the dressing;
b) the flow rate of irrigant fluid and/or wound exudate;
c) the temperature to which the point of supply of thermal energy to apparatus is raised;
d) the thermal insulation of the system in which the fluid recirculates and heat is conducted to the wound; and/or
e) the nature of the heater.

In examples of direct conductive contact of the irrigant and/or wound exudate with a heater and/or conductively heated component of the apparatus flow path, the heater may be or be connected to a heat exchanger mounted in conductive contact with irrigant and/or wound exudate at an appropriate point in the system in which the fluid recirculates and heat is conducted to the wound.

The heat exchanger may comprise an array of thermally conductive extended surfaces, such as fins, baffles or other like structures of conductive material in a more convoluted form with a relatively large surface area.

These transfer thermal energy when a temperature drop is applied over them, mounted in conductive contact with irrigant and/or wound exudate, with spaces therebetween such that wound irrigant and/or wound exudate may recirculate through the spaces.

Alternatively, where appropriate it may be provided in the form of a like array of conductive hollow structures, such as pipes, tubes or other like structures in the apparatus flow path, through which a heat exchanger fluid recirculates and transfers heat from a heat source to be conducted to the wound.

The array of conductive hollow structures may consist essentially of small apertures or pores that may form such bores, channels, conduits and/or passages through a heated metal sinter, such as one of e.g. stainless steel, mounted in conductive contact with irrigant and/or wound exudate in the apparatus flow path, through which the fluid recirculates, so that heat is conducted to the wound.

Such a heat exchanger may be outside the wound space and the backing layer or within the wound space and under the backing layer. If outside the wound space and the backing layer, it is preferably as close to the wound dressing backing layer as possible.

This is especially the case where the apparatus of the invention for irrigating, supplying thermal energy to and cleansing wounds is intended to maintain the wound at or near normothermic temperatures, since the heating must always pass to the wound through heat transfer via the irrigant and/or wound exudate recirculated through the wound space, and the longer the connection to the inlet pipe(s) on the wound dressing and the dwell time of the irrigant therein, the greater the undesired loss of heat from the irrigant fluid. It may be mounted outside the backing layer, e.g. 6 to 90 mm from the wound bed, e.g. on an inlet pipe and/or a fluid recirculation tube.

Where the heat exchanger is mounted outside the wound space and the backing layer, and transfers heat from a heat source to wound irrigant and/or wound exudate recirculating through the space, to be conducted to wound, the apparatus flow path, through which irrigant and/or wound exudate recirculates, at an appropriate point in the heat exchanger may be provided in the form of a conductive hollow structure in convoluted form with a relatively large surface area.

This transfers thermal energy from the heater and/or a heat exchanger fluid recirculated in conductive contact with it to the irrigant to be conducted to the wound.

In examples of such conductive contact of the irrigant and/or wound exudate with a heater and/or heat exchanger mounted, the apparatus flow path may be in convoluted form with a relatively large surface area, such as one or more pipes, tubes or other like structures, as appropriate 'in parallel' and/or with spaces therebetween, in the form of a spiral, helix or spiral helix, or loop or a more convoluted form, e.g. a meandering, tortuous, winding, zigzag, serpentine or boustrophedic (i.e. in the manner of a ploughed furrow) pattern, in particular a conductive hollow spiral.

Such a part of the flow path of the apparatus may be in direct conductive contact with a heater and/or conductively heated component, e.g. a conductive hollow spiral part of the flow path of the apparatus may within a moulded disc-shape housing defined by a film, sheet or membrane that a) has a heater and/or conductively heated component in direct conductive contact with and on at least one surface of the conductive hollow spiral part of the flow path, e.g. an electrically heated element mounted in an insulated so-called clamshell case, or b) contains a heat exchanger fluid recirculated between spaces between turns of the spiral to which it is applied.

A pre-formed spiral of tubing is housed in the heater case, which is preferably a rigid integer for convenient handling, which is then closed.

An apparatus flow path in a heat exchanger in the form of a helix or spiral helix, or loop or a more convoluted form, may also be in direct conductive contact with and within an appropriate moulded housing similarly provided in a form which transfers thermal energy from a heater and/or a heat exchanger fluid recirculated in conductive contact through it.

Alternatively, where appropriate, a flow path through which a heat exchanger fluid recirculates, e.g. a pre-formed spiral of tubing, may lie in spaces between and/or adjacent to turns or 'in parallel' arms of the apparatus flow path, and so transfer heat from a heat source to the irrigant and/or wound exudate flow. The whole may be loaded into a heater case, which is then closed. The flows of the heat exchanger fluid and the irrigant may be in a co- or preferably counter-current direction.

In all embodiments, the case has entry and exit apertures, holes, openings, orifices, slots, channels and/or conduits, e.g. in the edge extending between the faces of the case, through which the irrigant tubing passes, and into which it may be sealed or otherwise attached, for example by heat-sealing, and where it may be connected to other integers of the flow path.

Rather than using tubing, e.g. a conductive hollow spiral to define a tortuous path through which the irrigant is forced to flow in part of the flow path of the apparatus within a heat exchanger, it may be recirculated in conductive contact through one or more channels, conduits or passages or other like structures, as appropriate 'in parallel' and/or with spaces therebetween.

It or they may be in the form of a spiral, loop or a more convoluted form, e.g. a meandering, tortuous, winding, zig-zag, serpentine or boustrophedic (i.e. in the manner of a ploughed furrow) pattern, as appropriate 'in parallel' and/or with spaces therebetween.

This shape arrangement may, e.g. be made by sealing two flexible films, sheets or membranes together along lines of contact to form a convoluted flow path within a sealed chamber. This flow path is defined by one or more channels, conduits or passages or other like structures in a tortuous path through which the irrigant is forced to flow in part of the flow path of the apparatus, in particular in a boustrophedic (i.e. in the manner of a ploughed furrow) pattern. It may be made by sealing by a suitable method (e.g. radio frequency or impulse heat welding.

It or each is in conductive contact, preferably throughout its length, with a heater on at least one surface of the films defining the part of the flow path, e.g. an electrically heated element. The whole may be appropriately mounted in a case, bag, chamber or pouch of conventional type, such as a pouch or other structure, e.g. of polymer, which can contain the heater and/or heat exchanger, which is preferably a rigid integer to provide for convenient handling.

Alternatively, where appropriate, a flow path through which a heat exchanger fluid recirculates may be made to lie in spaces between and/or adjacent to turns or 'in parallel' arms of the apparatus flow path, and so transfer heat from a heat source to the irrigant and/or wound exudate flow. The whole may be appropriately housed in a case, bag, chamber or pouch of conventional type, as above. The flows of the heat exchanger fluid and the irrigant may be in a co- or preferably counter-current direction.

In all embodiments, the or each channel, conduit or passage or other like structure, will as appropriate at its inlet and outlet communicate with and be connected to a tube, pipe, duct or other like structure which in turn communicates with and is connected to other integers of the flow path, e.g. an irrigant feed pump.

The case, bag, chamber or pouch of conventional type, as referred to above has at least one entry and exit aperture, hole, opening, orifice and/or slot, through which the tubes, pipes, ducts or other like structures pass, and into which they may be sealed or otherwise attached, for example by heat-sealing.

For convenient handling in use, the case, bag, chamber or pouch of conventional type is adapted to fit as closely as possible into a receiving aperture, hole, opening, orifice and/or slot in a heat source to transfer heat to the irrigant in the apparatus flow. For example, the flat structures described by way of example above as suitable for use in this integer of the present invention may be sandwiched between parallel electrically heated plates.

It is preferably locked in position such that it cannot be dislodged accidentally in normal use, but can easily be removed when required.

For convenient handling in use, the heating device itself, into which the pouch is inserted, may be mounted securely on the patient and/or the wound dressing (if it is as close as possible to, e.g. 6 to 900 mm from the wound bed, e.g. on an inlet pipe and/or a fluid recirculation tube to reduce undesired loss of heat from the irrigant).

The means for providing thermal energy to the fluid in the wound may suitably comprise one or more such heater and/or heat exchanger modules connected in series and/or in parallel arms of the apparatus flow path.

Some of the factors likely to affect heat transfer in all embodiments of the exchanger are the temperature of the heater element, the structure and material appropriate to the heat exchanger and any heat exchanger fluid, the wall thickness and surface area in contact with the heater of any pipe, tube, channel, conduit, passage or other like structure, the length of irrigant flow path and the irrigant linear flow rate, the length of any heat exchanger fluid and any heat exchanger fluid flow rate, and whether any heat exchanger fluid and the irrigant flow are in co- or counter-current directions, as will be apparent to the skilled person.

The structure for holding irrigant in contact with the heater may suitably be a pipe, tube, channel, conduit, passage or the like. Such a structure may be a pipe, tube, channel, conduit, passage or the like on and integral with a face of the heater, which may be, e.g. an electrically heated plate, so that the irrigant and/or wound exudate recirculates in direct conductive contact with the heater in the heat exchanger. Alternatively or additionally, it may be in the form of a discrete pipe or tube permanently or releasably attached to at least one face of the heater, which again may be, e.g. at least one electrically heated plate, so that the irrigant and/or wound exudate recirculates in indirect conductive contact with the heater in the heat exchanger.

In either case, the walls of any pipe, tube, channel, conduit, passage or other like structure for irrigant in contact with the heater may suitably be no more than 600 micron thick. Where it is in contact with any pipe, tube, channel, conduit, passage or other like structure for heat exchanger fluid the combined thickness of the walls may suitably be 10 to 500 micron. When heat exchanger fluid and the irrigant flow are in counter-current directions, the thickness may be increased.

The surface area of any pipe, tube, channel, conduit, passage or other like structure for irrigant and/or wound exudate flow in contact with the heater or any pipe, tube, channel, conduit, passage or other like structure for a heat exchanger fluid (including those in a heated metal sinter) may suitably be no less than 100 mm$^2$, such as 625 to 2500 mm$^2$, e.g. up to 6400 mm$^2$.

Any pipe or tube, or any films, sheets or membranes sealed together along lines of contact to form a convoluted irrigant flow path, such as a channel, conduit, passage or other like structure may be of thermoplastic polyurethane or PVC but other materials may be used (e.g. thermoplastic elastomers), provided they are of suitable strength and flexibility and/or rigidity to provide for convenient handling, cleared for medical use and fulfil the desired performance specification.

The length of irrigant flow path, such as in the structures described by way of example above as suitable for use in this integer of the present invention may suitably be no less than 10 mm, such as 25 to 1600 mm, e.g. up to 2500 mm in the case of a 1.5×2.7 mm tube with flow rates of up to 400 ml/hr, up to 750 mm in the case of a similar channel defined by two welded films, and up to 360 mm in the case of a similar channel integral with a heater face as described hereinbefore, depending on particular components and/or materials that are used and on the surface area noted above.

For larger surface area of any pipe, tube, channel, conduit, passage or other like structure for irrigant flow, the length of irrigant flow path, e.g. in the structures described above may suitably be more than 2500 mm, such as (by way of example only) 4000 mm.

The volume flow rate of irrigant and/or wound exudate in recirculation through the means for providing thermal energy to the fluid in the wound may suitably and typically be the same as in the rest of the system in which the fluid recirculates, as described below. That is, of the order of 1 to 10 ml/cm$^2$/24 hour, where the cm$^2$ refers to the wound area, e.g. 1 to 750 ml/cm$^2$/hour, such as 1 to 500 ml/hr.

However, the cross-sectional area of any pipe, tube, channel, conduit, passage or other like structure for irrigant in the means for providing thermal energy to the fluid may be adjusted to increase or decrease the irrigant linear flow rate for the desired performance specification. To achieve the target temperature at the heater outlet, the irrigant linear flow rate in a typical heat exchanger with the irrigant flow path in the structures described above may suitably be 1 to 600 mm/s, e.g. up to 370 mm/s.

The surface area and the irrigant linear flow rate and length of irrigant flow path all depend inter alia on the particular target wound temperature and temperature at the heater outlet. Those noted above are generally suitable for use in this integer, where the temperature of the wound is to be held within a range of temperatures such as 34 to 40, preferably 35 to 39, and optimally 36 to 38° C. at the wound bed, preferably at normothermic temperatures, throughout the use of the present apparatus for irrigating, supplying thermal energy to and cleansing wounds.

Depending inter alia on the particular target wound temperature and the loss of heat from the irrigant between the means for providing thermal energy to the fluid and the wound dressing (especially if it is not as close as possible to, e.g. more than 6 to 900 mm from the wound bed), the temperature of irrigant leaving the heater will often conveniently be fixed at 39° C.+/−3° C., independently of flow rate, in particular to maintain an at or near normothermic temperature within the dressing, especially for chronic wounds.

The exit temperatures may of course be adjusted to increase or decrease wound temperatures, by adjusting the foregoing parameters, such as increasing or decreasing the irrigant linear flow rate for the desired temperature specification.

For example, with the flat structure heating pouch design described by way of example above as suitable for use in this integer and electrical heater (heating from only one side) it was found possible to maintain an irrigant temperature at the heater outlet of ~37° C. at irrigant rates of up to ~400 ml/hr.

This allows the liquid entering the wound to be as close as possible to the patient core temperature of ~37° C., and so help maintain normothermia. The area of pouch in contact with the heater was ~750 mm$^2$. To achieve the target temperature at the heater outlet at the highest flow rate, the heater was required to operate at a temperature of approximately 42° C.

All the foregoing means for providing thermal energy to the fluid and the wound dressing are especially (but not exclusively) suited to direct conductive contact of the irrigant and/or wound exudate with a heater and/or other conductively heated component. Various embodiments of heaters as a component of the apparatus flow path of the present apparatus for irrigating, supplying thermal energy to and cleansing wounds will now be described in detail hereinafter.

Examples of conductive heaters include:

a) an electric heater mounted in conductive contact with irrigant and/or wound exudate (but electrically insulated from the fluid and the system in which the fluid recirculates and heat is conducted to the wound).

The heater may inter alia comprise:

i) an array of electrically resistive but conductive wires, fibres, filaments, strands or other like structures that generate thermal energy when a voltage drop is applied over them.

The array may be a parallel array with spaces therebetween, and the wound irrigant and/or wound exudate may recirculate through the spaces.

Alternatively, where appropriate it may be provided in the form of non-woven or woven fabric, such as a woven layer or sheet. This may as appropriate be used essentially as a flat sheet or membrane of material in a more convoluted form, e.g. conformed to the form of other structures such as pipes, tubes, etc. in the apparatus flow path, as a duct, sheath, or casing, or other like structure.

Depending on any pressure differential across it may require other materials on or in it to stiffen, reinforce or otherwise strengthen it.

The material of the heater may have a positive or (less preferably) a negative thermal coefficient of resistance.

A control feedback circuit is needed with a negative coefficient of resistance for temperature regulation.

Materials that are described by way of example herein to be suitable for use in this aspect of the present invention will be capable of this function.

Depending on other components and/or materials that are present, examples of suitable materials include carbon fibres and fabric, such as a woven layer or sheet, which may as appropriate be made essentially of carbonised acrylate, such as polyacrylonitrile and copolymers thereof.

ii) an electrically insulating flat sheet or membrane substrate that has sites on its surface that are connected by an array of electrically resistive but conductive tracks, traces, outlines, or other like structures, e.g. filled channels, conduit and the like, and, e.g. etched foil, which generate thermal energy when a voltage drop is applied over them.

The array may be a parallel array with spaces therebetween, connected together at each end, or comprise or consist essentially of one or more such integers in a spiral, or in a meandering, tortuous, winding, zigzag, serpentine or boustrophedic (i.e. in the manner of a ploughed furrow) pattern.

Examples of suitable materials for the array of electrically resistive but conductive tracks, traces, outlines, or other like structures include carbon and/or metals, such as Thermion™, a nickel-coated non-woven carbon fabric and resistance heating alloys, such as Kanthal™, Alkrothal™, Nikrothal™, and Nifethal™.

For the electrically insulating flat sheet or membrane substrate, suitable materials include PTFE, polyamides, and materials such as aromatic polysulphones, polyethersulphones, polyetherether-sulphones, polyketones, polyetherketones; and polyetherether-ketones, and sulphonated derivatives thereof, and mixtures thereof; and epoxy resins.

The array of electrically resistive but conductive tracks, traces, outlines, or other like structures, may be generated by etching or engraving, e.g. with electron beam irradiation and/or with fluid chemicals.

Alternatively, where appropriate it may be provided by printing, imprinting, stamping or vapour deposition of conventional type.

iii) an array of electrically resistive but conductive, mutually connected thermocouples that are potentially capable of generating thermal energy by the Peltier effect when a voltage drop is applied over them.

The array may be a parallel array with spaces therebetween, and the wound irrigant and/or wound exudate may recirculate through the spaces.

Alternatively, it may be permanently or releasably attached to the surface of a substrate of the type described by way of example under ii) as suitable for use in this aspect of the present invention.

Depending on other components and/or materials that are present, examples of suitable materials include thermoelectric modules comprising pellets of bismuth telluride doped with selenium and antimony of different conductivity, the thermocouple pairs being connected in series and sandwiched between ceramic substrates.

In the Peltier effect when a voltage drop is applied over a thermocouple, one part potentially undergoes heating, and can thus supply thermal energy to the wound through a heat transfer medium (the irrigant).

The other part undergoes cooling and can thus act as a thermal pump from the ambient to the fluid irrigant and exudate in the apparatus flow path to the wound.

However, thermal energy transfer in this highly controllable manner requires orientation of the thermocouple array such that the side capable of gaining thermal energy by the Peltier effect is in conductive contact with the irrigant and/or wound exudate.

Examples of a) i) & ii) include a foam reservoir dressing, such as Allevyn (™, Smith & Nephew) and Tielle (™, Johnson & Johnson), having an electrical heater, mounted distally of the body on it.

b) an inductive heater element mounted in conductive contact with irrigant and/or wound exudate (but electrically insulated from the fluid and the system in which the fluid recirculates and heat is conducted to the wound).

The heater may inter alia comprises a piece of ferromagnetic material, such as magnetic stainless steel in conductive contact with irrigant and/or wound exudate, and an inductive source that will be adjacent (but not necessarily attached) to the dressing in use, but may otherwise be remote from the wound).

Examples of the latter include a ferromagnetic coil, spiral, helix or spiral helix, or loop or a more convoluted form, e.g. a meandering, tortuous, winding, zigzag, serpentine or boustrophedic (i.e. in the manner of a ploughed furrow) pattern, in particular in one plane, of an inductive often highly conductive material, connected to an alternating electrical potential source.

This is potentially capable of generating thermal energy in the core when a varying potential is applied to the coil, spiral or spiral helix, or loop or a more convoluted form.

This is often at mains voltage and frequency, although a range of either may be used.

c) a heater mounted in conductive contact with irrigant and/or wound exudate to which it transfers thermal energy to the fluid in recirculation from a heat source within it, which is a fuel cell.

In this, atmospheric oxygen and/or other molecules oxidise one or more species of fuel molecules, often in a catalytic bed.

Examples of fuel materials that have a strong oxidation exotherm include gases, where the gaseous phase of the aerosol system is air and a fuel gas, such as hydrogen or an alkane, such as methane, ethane and butane.

The catalyst is often solid particulates, such as composites of copper and rare earth oxides, such as optionally samaria doped ceria. comprised in a crystalline material for convenient handling; or platinum powder coated onto carbon paper or cloth.

d) a heater mounted in conductive contact with irrigant and/or wound exudate to which it transfers thermal energy to the fluid in recirculation from a heat source within it, which is a material that undergoes a highly exothermal phase change.

Examples of d) include i) a heater containing materials that undergo a highly exothermal crystallisation or solidification phase change, such as supersaturated solutions of chemicals, such as metal ion salts.

Sodium thiosulphate is a source of a strong crystallisation exotherm, as is sodium acetate solution.

The fluid or solid material is often comprised in one or more conformable hollow bodies.

These may be defined by, for example a polymer film, sheet or membrane, such as a bag, chamber, pouch or other structure, of the backing layer, e.g. of polymer film, for convenient handling.

In the case where the heat source is in the form of a crystallisation system, such as one based on sodium thiosulphate, the bag, chamber, pouch or other structure is often provided with a source of mechanical shock that is appropriate for inducing crystallisation.

Examples include a catastrophically resiliently flexible or stiff metal button, such as one of e.g. aluminium or stainless steel.

Such heaters are less preferred than an electrical heater, since electrical heating can give constant heating intensities in a highly controllable manner. In contrast, a strong crystallisation or solidification exotherm is less controllable or constant.

ii) a heater containing materials that undergo an exothermal condensation phase change, i.e. from gaseous or volatile products, such as the Freon hydrocarbon series to liquids. Preferred materials include, in particular those that condense at or near normothermic temperature. Such a heater of the irrigant fluid and/or wound exudate may be operated as a heat pump that absorbs thermal energy, e.g. from the environment of a component of the apparatus flow path into the component of the apparatus flow path.

In examples of a) direct electromagnetic irradiation at an appropriate wavelength, e.g. infrared and/or near infrared from a radiative heater of the irrigant fluid and/or wound exudate; and/or b) electromagnetic irradiation from a radiative heater of a component of the apparatus flow path that absorbs electromagnetic irradiation at an appropriate wavelength, e.g. infrared and/or near infrared and is in direct conductive contact with the irrigant and/or wound exudate.

the heater usually works at such temperatures as will deliver 34 to 40, preferably 35 to 39, and optimally 36 to 38° C. at the wound bed.

Examples of sources of direct or indirect electromagnetic irradiation of the irrigant fluid and/or wound exudate at an appropriate wavelength include infrared and/or near infrared from a radiative heater.

In the apparatus the type and materials of the heater will be largely determined by its specific function and the wavelengths and intensities to be applied to the fluid within the far infrared, mid infrared or near infrared spectrum, and its position in the apparatus of the invention.

Examples of suitable wavelengths to apply to the fluid include:

for the far infrared, 4 to 1000 micrometre,
for the mid infrared, 1.4 to 4 micrometre, and
for the near infrared, 0.75 to 1.5 micrometre.

Examples of suitable levels of intensity include those conventionally used in medical applications and known to the skilled person.

The higher end of these ranges are potentially more suitable for hospital use, where relatively high intensity infrared or near infrared irradiation at relevant wavelengths may be used safely under professional supervision.

Such a device may also suitably be one that is capable of pulsed, continuous, variable, and/or automated and/or programmable operation.

Examples include a) a radiative heater that is an incandescent filament lamp, light or other like structure, which is a source of radiation at relevant wavelengths to be applied to the fluid, e.g. infrared or near infrared irradiation. Examples of a) include a heater that is a small infrared lamp, mounted on an infra-red transparent dressing backing layer.

b) a radiative heater that is a high-thermal energy, high-intensity LED (light emitting diode) or other like structure, which is a source of radiation at relevant wavelengths to be applied to the fluid, e.g. infrared or near infrared irradiation.

c) a radiative heater that is a high-thermal energy, high-intensity source of radiation at relevant wavelengths to be applied to the fluid, e.g. infrared or near infrared irradiation.

The type and materials of the heater will be largely determined by its specific function and the wavelengths and intensities to be applied to the fluid within the spectrum, and its position in the apparatus of the invention.

d) Any r.f. and/or microwave frequency signal generator may be used provided temperatures at the wound do not exceed 38 to 40° C., and optimally 36 to 38° C.

Examples of sources of direct or indirect electromagnetic irradiation of the irrigant fluid and/or wound exudate at an appropriate wavelength also include radio-frequency e.m.r. in a range of 3 to 300 MHz, such as 10 to 100 MHz, such as 20 to 50 MHz.

Examples of preferred frequencies include microwave frequencies, using a microwave magnetron, in a range such as 1 to 300 GHz, such as 1 to 100 GHz, e.g. 1 to 50 GHz.

It will be appreciated that at these frequencies, in the range of microwave frequencies in particular, thermal energy is not just transferred to the fluid by simply being absorbed by the fluid and conducted to the wound. It is induced in the molecules in the fluid in the wound by radiation at an optimum frequency for such materials.

In all the above radiative heaters of the irrigant fluid and/or wound exudate, the electromagnetic irradiation from a radiative heater may pass into the fluid in the flow path directly, usually through a 'window' that is transparent to the relevant wavelengths to be applied to the fluid.

Amongst those materials that are suitable are glass; carbon fibres (which may be in a parallel array with spaces therebetween) and carbon fabric, such as a woven layer or sheet.

These may as appropriate be made essentially of carbonised acrylate, such as polyacrylonitrile and copolymers thereof; and various well-known polymers.

The transmissive structures may, alternatively or additionally, effectively be in the form of optical fibre(s) or waveguides of conventional type, e.g.

a) a tube, pipe, duct, fibre, filament, strand or other like structure, e.g. of carbon or the materials mentioned above, which is transparent to the relevant wavelengths to be applied to the fluid, b) coated, enclosed or enveloped by a coating, layer, sheet, skin or concentric tube, pipe, duct, sheath, or casing, or other like structure, of material on its outer face that is opaque and reflective to the relevant wavelengths.

These may pass at any relevant position along the apparatus flow path into the apparatus flow path where the heat is desired to be applied.

In one embodiment, they will pass under and/or through the backing layer of the dressing.

The transmissive structures may effectively be in the form of optical fibre(s) formed by a) at least one inlet pipe and/or fluid supply tube and/or at least one outlet pipe and/or fluid offtake tube, which passes through and/or under the wound-facing face, and is transparent or translucent to the relevant wavelengths to be applied to the fluid in the wound, and preferably to those that are optimum for wound healing, b) coated, enclosed or enveloped by a coating, layer, sheet, skin or concentric tube, pipe, duct, sheath, or casing, or other like structure, of material on its outer face that is opaque and reflective to the relevant wavelengths.

An advantage of such wound dressings is that these optical fibres may also serve as diagnostic 'keyholes' into the dressing to the wound bed in order to inspect the wound and assess its status. This is a significant advantage, in particular in chronic wounds.

As noted above, radiative energy may be absorbed by a component of the apparatus flow path that absorbs electromagnetic irradiation at an appropriate wavelength, e.g. infrared and/or near infrared and is in direct conductive contact with the irrigant and/or wound exudate.

Thus a radiative heater may be radiatively connected to a component of the apparatus flow path that absorbs electromagnetic irradiation at an appropriate wavelength, e.g. infrared and/or near infrared and is in direct conductive contact with the irrigant and/or wound exudate, e.g. by an air gap, the component containing a suitable absorbent and transmissive structure, e.g. an aqueous fluid, such as a hydrogel, that conducts heat through it to the irrigant fluid.

The temperature of the wound is generally held within a range of temperatures such as 34 to 40, preferably 35 to 39, and optimally 36 to 38° C. at the wound bed.

However, this may not provide a system for optimum performance of the wound healing process. It may be desirable, in particular in chronic wound dialysis, with relatively high concentrations of materials that are deleterious to wound healing, that the interior of the wound dressing is more beneficially maintained at a temperature that degrades such molecules in the fluid in the wound, e.g. at appropriate optimum degradation temperatures for such materials, rather than at normothermic temperature.

Other molecules involved in wound processes that are detrimental to wound healing include or gaseous or volatile by-products, such as carbon dioxide.

The irrigant may be warmed to a temperature that tends to degrade and/or outgas such molecules. The degradation or outgassing temperature of each detrimental gas, such as carbon dioxide, in aqueous media is either known or may readily be calculated.

Accordingly, another type of this apparatus of the invention for irrigating, supplying thermal energy to and cleansing wounds is provided with means for maintaining the wound at or near a temperature that is deleterious to molecules that are detrimental to wound healing.

As noted above, other physiologically active components of the wound cells are beneficial in promoting wound healing and may be stimulated by radiation on the wound under the backing layer.

Where these are enzymes, growth factors and anti-inflammatories, cell mitochondria and other physiologically active components of the exudate from a wound, examples of suitable wavelengths and intensities to apply to the fluid in the wound to favour such materials an cell components will be known to the skilled person.

As regards the apparatus flowpath, the means for flow switching between supply and recirculation may take any form that enables the wound simultaneously to be a) put into communication with the fluid reservoir but
b) closed to the fluid recirculation tube, and
c) vice versa.

Thus, if there is only one inlet pipe that passes through and/or under the wound-facing face of the wound dressing, the fluid reservoir is connected by the fluid supply tube to the flow path via means for flow switching as desired the into a fluid recirculation tube or a fluid offtake tube.

In this case, the means for flow switching between supply and recirculation may be a regulator, such as a T-valve.

This is connected in turn to two parts of a fluid recirculation tube or a fluid offtake tube and the fluid supply tube, such that the desired flow switching between supply and recirculation is achieved.

If there are two or more inlet pipes, these may be connected respectively to a fluid supply tube or fluid recirculation tube, respectively having a first regulator and a second regulator, such as a valve or other control device for admitting fluids into the wound.

The desired flow switching between supply and recirculation is achieved by respectively having the first regulator open when the second regulator is shut, and vice versa.

The means for bleeding the flowpath may be situated in any appropriate part of the apparatus that is in contact with the irrigant and/or wound exudate, but is usually within the offtake and/or recirculation tubes.

However, it is often as far downstream of and away from the reservoir and the fluid supply tube as possible, so that it may be used to prime the whole of the flowpath from the fluid reservoir via the fluid supply tube.

It may be a regulator, such as a valve or other control device, e.g. a T-valve that is turned to switch between bleed and recirculation, for bleeding fluids from the apparatus, e.g. to a waste reservoir, such as a collection bag.

Alternatively, flow switching between supply and recirculation may not be desired, but rather concomitant bleeding and/or recirculation is desired.

The latter may occur when the volume of irrigant and/or wound exudate in recirculation is increased by continuing addition to it of a) wound exudate, and/or
b) fluid passing from a cleansing fluid through a selectively permeable integer, for example in a system such as a dialysis unit.

The means for bleeding the offtake and/or recirculation tubes may then be provided in the form of a regulator, such as a simple valve or other control device for admitting or blocking the passage of irrigant and/or exudate through a bleed line branching from the recirculation path.

The means for fluid cleansing may as desired be a 'single-phase system'.

In this, the circulating fluid from the wound and the fluid reservoir passes through a self-contained system in which materials deleterious to wound healing are removed and the cleansed fluid, still containing materials that are beneficial in promoting wound healing, is returned via the recirculation tube to the wound bed. Such systems are described in further detail hereinafter in connection with the means for fluid cleansing.

Alternatively, where appropriate it may be provided in the form of a two-phase system, such as a dialysis unit, or a biphasic liquid extraction unit.

In this, the circulating fluid from the wound and the fluid reservoir passes through a system in which the fluid recirculates in indirect or (less usually, direct) contact with a second fluid (dialysate) phase, more usually a liquid.

Materials deleterious to wound healing are removed into the second phase, and the cleansed fluid, still containing materials that are beneficial in promoting wound healing, is returned via the recirculation tube to the wound bed. Such systems are described in further detail hereinafter in connection with the means for fluid cleansing.

In use, typically, the means for flow switching between supply and recirculation tubes is set to admit fluid into the wound from the fluid reservoir but to close the wound to the fluid recirculation tube.

Then, any means for bleeding the offtake and/or recirculation tubes are is opened and the device for moving fluid through the wound and means for fluid cleansing is started.

The capacity of the apparatus flow path and the flow rate of irrigant and/or wound exudate from the wound will largely determine whether it is appropriate to run the device to prime the apparatus throughout the whole length of the apparatus flow path, i.e. to displace any existing fluid reservoir (often air) from the fluid recirculation path, and for how long it should be run.

Typically, there is a preponderance of irrigant from the fluid reservoir over wound exudate in recirculation, so that use of the device for moving fluid through the wound is appropriate for this purpose.

It is allowed to run until the apparatus is primed throughout the whole length of the apparatus flow path.

Then, typically the means for bleeding the offtake and/or recirculation tubes is closed, and the means for flow switching between supply and recirculation tubes is set to close the wound to the fluid reservoir but to admit fluid into the wound from the fluid recirculation tube.

If the means for fluid cleansing is a two-phase system, such as a dialysis unit, or a biphasic extraction unit, the cleansing fluid is typically set in motion in contact with the surface of the selectively permeable integer, for example the polymer film, sheet or membrane. Of course, the cleansing fluid may less usually be static, and then this step is omitted.

As noted below in more detail, the volume of irrigant and/or wound exudate from the wound in recirculation may be increased by continuing addition to it of
a) wound exudate, and/or
b) fluid passing from a cleansing fluid through a selectively permeable integer, for example the polymer film, sheet or membrane of a two-phase system, such as an dialysis unit.

Additionally or alternatively, it may be desired to apply a negative pressure to the wound by means of a device for moving fluid through the wound and means for fluid cleansing applied to the fluid in recirculation in the fluid recirculation tube downstream of and away from the wound dressing.

In such case, it may be desirable to provide a system in which concomitant bleeding and/or recirculation is possible, and to make the necessary adjustments to maintain the desired balance of fluid in recirculation by means of the means for bleeding the offtake and/or recirculation tubes.

The volume of irrigant and/or wound exudate from the wound in recirculation may be decreased by continuing loss from it of fluid passing from a cleansing fluid through a selectively permeable integer, for example in a system such as a dialysis unit.

Additionally or alternatively, it may be desired to apply a positive pressure to the wound by means of a device for moving fluid through the wound and means for fluid cleansing applied to the fluid in recirculation in the fluid recirculation tube upstream of and towards the wound dressing.

The means for flow switching between supply and recirculation may be similarly provided in a form in which concomitant supply and/or recirculation is possible, and to make the necessary adjustments to maintain the desired balance of fluid in recirculation by means of the means for flow switching.

It will be appreciated that where a positive or negative pressure is to be applied to the wound, at least one hollow body in the recirculation flow path to and from the wound bed should have sufficient resilience against the pressure to allow any significant compression or decompression of the irrigant fluid to occur.

In all embodiments of the apparatus, the type and material of such bodies (which are defined by a film, sheet or membrane) that are described by way of example herein to be suitable for use in the present invention will be largely capable of this function.

Thus, examples of suitable materials for bodies defined by a film, sheet or membrane, such as inlet or offtake and/or recirculation tubes and structures such as bags, chambers and pouches, filled with irrigant fluid, e.g. the backing layer of the wound dressing are suitably elastically resilient thermoplastic materials that are potentially capable of this function when pressure is applied in this way.

The present invention in this aspect provides several advantages.

One is that application of a positive pressure to the wound under the backing layer may make it possible to flood the tissue underlying the wound with one or more physiologically active components.

This may be effected in therapeutically active amounts, to promote greater wound healing than by treatment with the fluid physiologically active component(s) alone.

Such physiologically active components of the exudate that are beneficial to wound healing may be e.g. be enzymes or other species and may be supplied from the dialysate of a dialytic means for fluid cleansing.

It is believed that using the apparatus for irrigating, supplying thermal energy to and/or cleansing wounds of the present invention cyclically the effects may be further enhanced.

Such cyclical regimens for such further enhancement may be applied to
a) the flow direction, rate, positive or negative pressure,
b) nature of the circulating fluid (such as water, saline, etc.) and/or
c) the thermal energy applied to the wound bed over an extended period.

Circulating wound fluid aids in movement of biological signalling molecules involved in wound healing to locations in the wound bed that are favourable to the wound healing process and/or to cells that would otherwise not be exposed to them, e.g. in a highly exuding wound.

This is especially the case in those embodiments of the apparatus of this first aspect of the present invention for irrigating, supplying thermal energy to and/or cleansing wounds where there is an inlet or outlet manifold from which tubules radiate and run to the wound bed to end in openings that deliver and collect the fluid directly from the wound bed over an extended area.

Such materials include cytokines, enzymes, nutrients for wound cells to aid proliferation, oxygen, and other molecules that are beneficially involved in wound healing, such as growth factors, and others having beneficial effects (which may be further enhanced) in causing chemotaxis.

In all embodiments of the apparatus of this first aspect of the present invention for irrigating, supplying thermal energy to and/or cleansing wounds, a particular advantage is the tendency of the wound dressing to conform to the shape of the bodily part to which it is applied.

The wound dressing comprises a backing layer with a wound-facing face which is capable of forming a relatively fluid-tight seal or closure over a wound and at least one inlet pipe for connection to a fluid supply tube or recirculation tube, which passes through and/or under the wound-facing face, and and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure.

The term 'relatively fluid-tight seal or closure' is used herein to indicate one which is fluid- and microbe-impermeable and permits a positive or negative pressure of up to 50% atm., more usually up to 15% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to irrigating, supplying thermal energy to and/or cleansing the wound across the area of the wound.

Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof;

polysiloxanes;

polyesters, such as polycarbonates;

polyamides, e.g. Nylon 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound.

It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound.

This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable).

This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

Where a vacuum, is applied to hold the wound dressing in place in a fluid-tight seal around the periphery of the wound-facing face of the wound dressing, the wound dressing may be provided with a silicone flange or lip to seal the dressing around the wound. This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose.

Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheathes, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheathes, wraps, stockings and hose that are a compressive fit over a limb wound to apply suitable pressure to it when the therapy is applied in this way.

Such means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound.

Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit.

It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound.

The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of a fluid recirculation tube and/or fluid supply tube (optionally or as necessary via means for forming a tube, pipe or hose, or nozzle, hole, opening, orifice, luer, slot or port for connection as a male member respectively to a mating end of a fluid recirculation tube and/or fluid supply tube (optionally or as necessary via means for flow switching between supply and recirculation) or a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The or each pipe will generally pass through, rather than under the backing layer.

In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid recirculation tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer.

The wound dressing may not comprise any integer under the backing layer in the wound in use, other than the ribs or ridges mentioned herein.

However, this may not provide a system to distribute irrigant over a sufficient functional surface area to irrigate the wound at a practical rate. To be suitable for use, in particular in chronic wound dialysis, with relatively high concentrations of materials that are deleterious to wound healing, it may be advantageous to provide a system where wound irrigant and/or wound exudate may be distributed more evenly, or pass in a more convoluted path under the dressing over the wound bed.

Accordingly, one form of the dressing is provided with a 'tree' form of pipes, tubes or tubules that radiate from an inlet manifold to the wound bed to end in apertures and deliver the circulating fluid directly to the wound bed via the apertures. Similarly, there is an outlet manifold from which tubules radiate and run to the wound bed to end in openings and collect the fluid directly from the wound bed.

The pipes, etc. may radiate regularly or irregularly through the wound in use, respectively from the inlet or outlet manifold, although regularly may be preferred. A more suitable layout for deeper wounds is one in which the pipes, etc. radiate hemispherically and concentrically, to the wound bed.

For shallower wounds, examples of suitable forms of such layout of the pipes, etc. include ones in which the pipes, etc. radiate in a flattened hemiellipsoid and concentrically, to the wound bed.

Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed. These may have a blind bore with perforations, apertures, holes, openings, orifices, slits or slots along the pipes, etc.

These pipes, etc. then effectively form an inlet pipe manifold that delivers the circulating fluid directly to the wound bed or outlet pipe or collects the fluid directly from the wound respectively.

It does so via the holes, openings, orifices, slits or slots in the tubes, pipes, tubules, etc. over most of the wound bed under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound.

Thus, for shallower wounds, examples of suitable forms of such layout of the tubes, pipes, tubules, etc. include ones that consist essentially of one or more of the tubes, etc in a spiral.

A more suitable layout for deeper wounds when the therapy is applied in this way may be one that comprises one or more of the tubes, etc in a helix or spiral helix.

Other suitable layouts for shallower wounds include one which have blind-bore, perforated inlet pipe or outlet pipe manifolds that circulate fluid in the wound when the dressing is in use.

One or both of these may be such a form, the other may be, e.g. one or more straight blind-bore, perforated radial tubes, pipes or nozzles.

Another suitable layout is one in which
an inlet pipe and/or outlet pipe manifold that delivers the circulating fluid directly to the wound bed or collects the fluid directly from the wound respectively
via inlet and/or outlet tubes, pipes or tubules,
and the inlet manifold and/or outlet manifold is formed by slots in layers permanently attached to each other in a stack, and
the inlet and/or outlet tubes, pipes or tubules are formed by apertures through layers permanently attached to each other in a stack.

(In FIG. 10a there is shown an exploded isometric view of such a stack, which is non-limiting.)

As also mentioned herein, the backing layer that is applied may be any that is appropriate to the present system of therapy and permits a positive or negative pressure of up to 50% atm., more usually up to 25% atm. to be applied to the wound.

It is thus often a microbe-impermeable film, sheet or membrane, which is substantially flat, depending on any pressure differential on it.

It often has a (generally uniform) thickness similar to such films or sheets used in conventional wound dressings, i.e. up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss.

Such a form of dressing would not be very conformable to the wound bed, and may effectively form a chamber, hollow or cavity defined by a backing layer and the wound bed under the backing layer.

It may be desirable that the interior of the wound dressing conform to the wound bed, even for a wound in a highly exuding state. Accordingly, one form of the dressing is provided with a wound filler under the backing layer.

This is favourably a resiliently flexible, e.g. elastomeric, and preferably soft, structure with good conformability to wound shape.

It is urged by its own resilience against the backing layer to apply gentle pressure on the wound bed.

The wound filler may be integral with the other components of the dressing, in particular the backing layer.

Alternatively, it may be permanently attached to them/it, with an adhesive film, for example, or by heat-sealing, e.g. to a flange or lip extending from the proximal face, so a not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other.

The wound filler may be or comprise a solid integer, favourably a resiliently flexible, e.g. elastomeric, and preferably soft, structure with good conformability to wound shape. Examples of suitable forms of such wound fillers are foams formed of a suitable material, e.g. a resilient thermoplastic. Preferred materials for the present wound dressing include reticulated filtration polyurethane foams with small apertures or pores.

Alternatively or additionally, it may be in the form of, or comprise one or more conformable hollow bodies defined by a film, sheet or membrane, such as a bag, chamber, pouch or other structure, filled with a fluid or solid that urges it to the wound shape.

The film, sheet or membrane, often has a (generally uniform) thickness similar to that of films or sheets used in conventional wound dressing backing layers.

That is, up to 100 micron, preferably up to 50 micron, more preferably up to 25 micron, and of 10 micron minimum thickness, and is often resiliently flexible, e.g. elastomeric, and preferably soft.

Such a filler is often integral with the other components of the dressing, in particular the backing layer, or permanently attached to them/it, with an adhesive film, for example, or by heat-sealing, e.g. to a flange Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, or preferably cellulosic gels, for example hydrophilic cross-linked cellulosic gels, such as Intrasite™ cross-linked materials.

Examples also include aerosol foams, where the gaseous phase of the aerosol system is air or an inert gas, such as nitrogen or argon, more usually air, at a small positive pressure above atmospheric; foams, including set aerosol foams, e.g. CaviCare™ foam, and solid particulates, such as plastics crumbs.

Of course, if the backing layer is a sufficiently conformable and/or e.g. an upwardly dished sheet, the backing layer may lie under the wound filler, rather than vice versa.

In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other.

In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a resiliently flexible, e.g. elastomeric, and preferably soft, hollow body defined by a film, sheet or membrane, such as a bag, chamber, pouch or other structure, with apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body may then be the circulating fluid in the apparatus.

The hollow body or each of the hollow bodies then effectively forms an inlet pipe or outlet pipe manifold that delivers the circulating fluid directly to the wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound.

Thus, for shallower wounds, examples of suitable wound fillers as a component of a wound dressing include ones that consist essentially of one or more conformable hollow bodies defining an inlet pipe and/or outlet pipe manifold that delivers the circulating fluid directly to the wound bed or collects the fluid directly from the wound.

A more suitable wound filler for deeper wounds when the therapy is applied in this way may be one which comprises one or more conformable hollow bodies defined by, for example a polymer film, sheet or membrane.

The latter at least partly surround(s) a solid integer, which may provide a system with better rigidity for convenient handling.

The wound filler under the backing layer may effectively form an inlet or outlet manifold with a direct connection between the inlet pipe(s) and outlet pipe(s) at the point at which they pass through and/or under the wound-facing face and the wound bed.

If not, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filler under the backing layer.

Less usually, the wound filler is an open-cell foam with pores that may form such bores, channels, conduits, passages and/or spaces through the wound filler under the backing layer.

Where the filler is or comprises one or more conformable hollow bodies defined by, for example a polymer film, sheet or membrane, it may be provided with means for admitting fluids to the wound bed under the wound dressing.

These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that circulate fluid in the wound when the dressing is in use, that are described hereinbefore, may be used under a wound filler under the backing layer.

In brief, suitable layouts include ones where one or both manifolds are annular or toroidal (regular, e.g. elliptical or circular, or irregular), optionally with blind-bore, perforated radial tubes, pipes or nozzles, branching from the annulus or torus; and/or in a meandering, tortuous, winding, zigzag, serpentine or boustrophedic (i.e. in the manner of a ploughed furrow) pattern, or defined by slots in and apertures through layers attached to each other in a stack.

The inlet and/or outlet tubes, the fluid recirculation tube and the fluid supply tube, etc. may be of conventional type, e.g. of elliptical or circular cross-section, and may suitably have a uniform cylindrical bore, channel, conduit or passage throughout their length.

Depending on the desired fluid volume flow rate of irrigant and/or wound exudate from the wound, and the desired amount in recirculation, suitably the largest cross-dimension of the bore may be up to 10 mm for large torso wounds, and up to 2 mm for limb wounds.

The tube walls should suitably thick enough to withstand any positive or negative pressure on them.

This is the case in particular if the volume of irrigant and/or wound exudate from the wound in recirculation is increased by continuing addition to it of wound exudate, and/or fluid passing from a cleansing fluid through a selectively permeable integer, for example the polymer film, sheet or membrane of a two-phase system, such as an dialysis unit. However, as noted below with regard to pumps, the prime purpose of such tubes is to convey fluid irrigant and exudate through the length of the apparatus flow path, rather than to act as pressure vessels. The tube walls may suitably be at least 25 micron thick.

The bore or any perforations, apertures, holes, openings, orifices, slits or slots along the pipes, etc. or in the hollow body or each of the hollow bodies may be of small cross-dimension.

They may then effectively form a macroscopic and/or microscopic filter for particulates including cell debris and micro-organisms, whilst allowing proteins and nutrients to pass through.

Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s).

The whole length of the apparatus for irrigating, supplying thermal energy to and/or cleansing wounds should be microbe-impermeable once the wound dressing is over the wound in use.

It is desirable that the wound dressing and the interior of the apparatus for irrigating, supplying thermal energy to and/or cleansing wounds of the present invention is sterile.

The fluid may be sterilised in the fluid reservoir and/or the rest of the system in which the fluid recirculates, including the means for fluid cleansing, by ultraviolet, gamma or electron beam irradiation. This way, in particular reduces or eliminates contact of internal surfaces and the fluid with any sterilising agent.

Examples of other methods of sterilisation of the fluid also include e.g. the use of ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide;

although the latter involve contact of internal surfaces and the fluid with the sterilising agent.

It may be desirable that the interior of the wound dressing, the rest of the system in which the fluid recirculates, and/or the wound bed, even for a wound in a highly exuding state, are kept sterile after the fluid is sterilised in the fluid reservoir, or that at least naturally occurring microbial growth is inhibited.

Thus, materials that are potentially or actually beneficial in this respect may be added to the irrigant initially, and as desired the amount in recirculation increased by continuing addition.

Examples of such materials include antibacterial agents (some of which are listed above), and antifungal agents.

Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate. may be added to adjust the pH, as may local analgesics/anaesthetics, such as lidocaine/lignocaine hydrochloride, xylocaine (adrenaline, lidocaine) and/or anti-inflammatories, to reduce wound pain or inflammation or pain associated with the dressing.

It is also desirable to provide a system in which physiologically active components of the exudate that are beneficial to wound healing are not removed before or after the application of fluid cleansing.

Examples include the passive deposition of materials that are beneficial in promoting wound healing, such as proteins, e.g. growth factors.

This may occur at any point at least one inlet or outlet pipe through at least one aperture, hole, opening, orifice, slit or slot.

The fluid contained in the hollow body may the deposition of materials that are beneficial in promoting wound healing, and consequent coating, a) may be added to the irrigant initially, and as desired the amount in recirculation increased by continuing addition, or b) may be used at any point or on any integer in the recirculation path in direct contact with the fluid, e.g. on the means for fluid cleansing or any desired tube or pipe.

Examples of coating materials for surfaces over which the circulating fluid passes include anticoagulants, such as heparin, and high surface tension materials, such as PTFE, and polyamides, which are useful for growth factors, enzymes and other proteins and derivatives.

The apparatus of the invention for irrigating, supplying thermal energy to and/or cleansing wounds is provided with means for admitting fluids directly or indirectly to the wound under the wound dressing in the form of a fluid supply tube to a fluid reservoir.

The fluid reservoir may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid.

The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body.

In all embodiments of the apparatus the type and material of the tubes throughout the apparatus of the invention for irrigating, supplying thermal energy to and/or cleansing wounds and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system dialysis unit, of the dialysate that moves into the circulating fluid in the apparatus.

When in contact with irrigant fluid, it should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, e.g. high-density polyethylene and polypropylene.

Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

The device for moving fluid through the wound and means for fluid cleansing may be any appropriate for this purpose, and may act at any appropriate point for this purpose.

It may apply a positive or negative pressure to the wound, although its prime purpose is to move fluid (irrigant from the fluid reservoir and/or wound exudate through the length of the apparatus flow path, rather than to apply a positive or negative pressure to the wound.

If applied to the fluid in recirculation in the fluid recirculation tube upstream of and towards the wound dressing and/or the fluid in the fluid supply tube towards the wound dressing (optionally or as necessary via means for flow switching between supply and recirculation), it will usually apply positive pressure (i.e. above-atmospheric pressure) to the wound bed.

Often the means for fluid cleansing is (most appropriately for its purpose) downstream of the wound dressing, and provides the highest resistance in the flow path. This is especially the case where the means for fluid cleansing is a single-phase system, e.g. with ultrafiltration through microapertures or micropores, thus enhancing applied positive pressure to the wound.

Where the device is applied to the fluid in recirculation in the fluid recirculation tube and/or the fluid in the fluid offtake tube downstream of and away from the wound dressing, it will usually apply negative pressure (i.e. below-atmospheric pressure or vacuum) to the wound bed.

Again, often the means for fluid cleansing is (most appropriately for its purpose) downstream of the wound dressing, and provides the highest resistance in the flow path, thus enhancing applied negative pressure to the wound.

The following types of pump may be used as desired:

reciprocating pumps, such as:

shuttle pumps—with an oscillating shuttle mechanism to move fluids at rates from 2 to 50 ml per minute;

diaphragm pumps—where pulsations of one or two flexible diaphragms displace liquid while check valves control the direction of the fluid flow.

piston pumps—where pistons pump fluids through check valves, in particular for positive and/or negative pressure on the wound bed;

rotary pumps, such as:

centrifugal pumps flexible impeller pumps—where elastomeric impeller traps fluid between impeller blades and a moulded housing that sweeps fluid through the pump housing.

progressing cavity pumps—with a cooperating screw rotor and stator, in particular for higher-viscosity and particulate-filled exudate;

rotary vane pumps—with rotating vaned disk attached to a drive shaft moving fluid without pulsation as it spins. The outlet can be restricted without damaging the pump.

peristaltic pumps—with peripheral rollers on rotor arms acting on a flexible fluid circulation tube to urge fluid current flow in the tube in the direction of the rotor.

vacuum pumps—with pressure regulators.

The type and/or capacity of the device will be largely determined by a) the appropriate or desired fluid volume flow rate of irrigant and/or wound exudate from the wound, and b) whether it is appropriate or desired to apply a positive or negative pressure to the wound bed, and the level of such pressure to the wound bed for optimum performance of the wound healing process, and by factors such as portability, power consumption and isolation from contamination.

Such a device may also suitably be one that is capable of pulsed, continuous, variable, reversible and/or automated and/or programmable fluid movement. It may in particular be a pump of any of these types.

In practice, even from a wound in a highly exuding state, such a rate of exudate flow is only of the order of up to 75 microlitres/cm$^2$/hr (where cm$^2$ refers to the wound area), and the fluid can be highly mobile (owing to the proteases present).

Exudate levels drop and consistency changes as the wound heals, e.g. to a level for the same wound that equates to 12.5-25 microlitres/cm$^2$/hr.

Where materials deleterious to wound healing are removed by a two-phase system (see below.), such as a dialysis unit, fluid is also potentially lost to the system through the means for fluid cleansing.

This may occur, e.g. through a dialysis polymer film, sheet or membrane which is also permeable to water, in addition to materials deleterious to wound healing.

The balance of fluid in recirculation may thus further decrease, but may be adjusted to minimise this undesired loss in a routine manner as described hereinbefore.

Hence, it will be seen that the circulating fluid from the wound will typically contain a preponderance of irrigant over wound exudate in recirculation from the fluid reservoir.

The type and/or capacity of the device will thus be largely determined in this respect by the appropriate or desired fluid volume flow rate of irrigant, rather than that of exudate, from the wound.

In practice, the 'normal' irrigation rate will be different for each dressing size, but the rate of flow of total irrigant and/or wound exudate will be of the order of 1 to 10 ml/cm$^2$/24 hour, where the cm$^2$ refers to the wound area, e.g. 1 to 5 ml/ cm$^2$/24 hour, such as 1 to 3.5 ml hr.

If wound temperatures a) above normothermic temperature are required, e.g. a temperature at or above 42° C., e.g. for the degradative removal of deleterious materials, or b) below normothermic temperatures are required, e.g. 32° C. to 35° C., e.g. for decreasing the inflammation of a wound, the necessary target temperature at the heater outlet may be achieved by adjusting parameters, such as increasing or decreasing the linear flow rate of the irrigant and/or any heat exchanger fluid or the temperature of the heater in a routine manner known to the skilled person.

It is desirable that the interior of the wound dressing and the rest of the system in which the fluid recirculates be flushed cyclically before and/or after use in treatment, to cleanse them, and it is convenient that this is effected by the device for moving fluid through the wound and means for fluid cleansing.

Accordingly, the device may deliver a flush cycle at an irrigation rate substantially greater than the 'normal' rate; this could typically be up to 650 ml/hr for the largest dressing size. It may be desirable therefore that the apparatus adjusts the heat energy delivered to the wound in accordance with the selected irrigant/exudate flow rates at any moment in time.

The volume of irrigant and/or wound exudate in recirculation may vary over a wide range, but will typically be e.g. 1 to 8 l. (for example for large torso wounds), 30 to 300 ml (for example for axillary and inguinal wounds), and 200 to 1500 ml for limb wounds when the therapy is applied in this way.

In practice, suitable pressures are of the order of up to 25% atm such as up to 10% atm. positive or negative pressure on the wound bed, the apparatus being operated as a closed recirculating system.

The higher end of these ranges are potentially more suitable for hospital use, where relatively high % pressures and/or vacua may be used safely under professional supervision.

The lower end is potentially more suitable for home use, where relatively high % pressures and/or vacua cannot be used safely without professional supervision, or for field hospital use.

The device may be a peristaltic pump or diaphragm pump, e.g. preferably a small portable diaphragm or peristaltic pump. These are preferred types of pump, in order in particular to reduce or eliminate contact of internal surfaces and moving parts of the pump with (chronic) wound exudate, and for ease of cleaning.

It may suitably be one that applies positive pressure to the wound and/or the means for fluid cleansing.

A preferred pump when the applied pressure is positive is a peristaltic pump, e.g. a small, portable peristaltic pump, mounted upstream of the means for fluid cleansing.

Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

The pump may suitably be one that applies negative pressure to the wound and/or the means for fluid cleansing.

A preferred pump when the applied pressure is negative is a diaphragm pump, e.g. a small, portable diaphragm pump, mounted downstream of the dressing or the means for fluid cleansing.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

The outlet from the dressing passes to the means for fluid cleansing for removal of materials deleterious to wound healing from wound exudate, and in turn to the fluid recirculation tube(s).

The apparatus of the invention for irrigating, supplying thermal energy to and/or cleansing wounds is provided with means for fluid cleansing, which may be a) a single-phase system, such as an ultrafiltration unit, or a chemical absorption and/or adsorption unit; or b) a two-phase system, such as a dialysis unit, or a biphasic extraction unit.

In the former, circulating fluid from the wound and the fluid reservoir passes through a self-contained system in which materials deleterious to wound healing are removed and the cleansed fluid, still containing materials that are beneficial in promoting wound healing are returned to the wound.

The single-phase system may be of any conventional type.

Examples of such include an ultrafiltration unit, such as a one in which the cleansing integer is a filter for materials deleterious to wound healing, for example a high throughput, low protein-binding polymer film, sheet or membrane which is selectively impermeable to materials deleterious to wound healing, which are removed and the cleansed fluid, still containing materials that are beneficial in promoting wound healing is passed by it.

The membrane may preferably be of a hydrophilic polymeric material, such as a cellulose acetate-nitrate mixture, polyvinylidene chloride, and, for example hydrophilic polyurethane.

Examples of less preferred materials include hydrophobic materials also including polyesters, such as polycarbonates, PTFE, and polyamides, e.g. nylon 6-6 and 6-10, and hydrophobic polyurethanes, and quartz and glass fibre.

It has microapertures or micropores, the maximum cross-dimension of which will largely depend on the species that are to be selectively removed in this way and those to which it is to be permeable.

The former may be removed with microapertures or micropores, e.g. typically with a maximum cross-dimension in the range of 20 to 700 micron, e.g. 20 to 50 nm (for example for undesired proteins), 50 to 100 nm, 100 to 250 nm, 250 to 500 nm and 500 to 700 nm.

The filter integer may be a flat sheet or a membrane of a polymeric material in a more convoluted form, e.g. in the form of elongate structure, such as pipes, tubules, etc.

The system may be a chemical adsorption unit, for example one in which a particulate, such as a zeolite, or a layer, e.g. of a functionalised polymer has sites on its surface that are capable of removing materials deleterious to wound healing on passing the circulating fluid from the wound and the fluid reservoir over them.

The materials may be removed, e.g. by destroying or binding the materials that are deleterious to wound healing, by, for example chelators and/or ion exchangers, degraders, which may be enzymes.

Examples of such also include less specific chemical adsorption units, for example one in which a physical absorbent, such as activated carbon or a zeolite, has non-specific sites on its surface that are capable of removing materials deleterious to wound healing on passing the circulating fluid from the wound and the fluid reservoir over them.

The cleansing integer, for example the polymer film, sheet or other chemical adsorption means, etc should of course be capable of removing materials deleterious to wound healing at a practical rate for a given capacity of the apparatus flow path and the flow rate of irrigant.

In the two-phase system, circulating fluid from the wound and the fluid reservoir in indirect or (less usually, direct) contact with a second fluid (dialysate) phase, more usually a liquid.

Thus, in one form, a biphasic liquid extraction unit, the second fluid phase is (usually) a liquid that is immiscible with the circulating fluid from the dressing, over a surface of which the circulating fluid passes in direct contact with the cleansing fluid. Materials deleterious to wound healing are removed into the dialysate, and the cleansed fluid, still containing materials that are beneficial in promoting wound healing, is returned via the recirculation tube to the wound bed.

Examples of such means for fluid cleansing include those wherein the second fluid (dialysate) phase is perfluorodecalin and like materials Alternatively, where appropriate it may be provided in a form in which the two fluids (recirculation fluid and dialysate) are separated by a significantly two-dimensional integer, for example a polymer film, sheet or membrane or hollow fibre or filament that is permeable to materials in the circulating fluid in the apparatus.

Again, materials deleterious to wound healing are removed into the dialysate, and the cleansed fluid, still containing materials that are beneficial in promoting wound healing, is returned via the recirculation tube to the wound bed.

In either form in which the two-phase system, such as a dialysis unit, is provided, in use typically the dialysate moves past the circulating fluid in the apparatus in a co- or preferably counter-current direction.

Pumps, such as peristaltic pumps, and/or valves control the direction of the two fluid flows.

However, the cleansing fluid may less usually be static, although this may not provide a system with sufficient (dynamic) surface area to remove materials deleterious to wound healing from wound exudate at a practical rate.

Typical dialysate flow rates in a dialytic means for fluid cleansing in the present apparatus for irrigating, supplying thermal energy to and/or cleansing wounds are those used in the conventional type of two-phase system, such as a dialysis unit for systemic therapy.

The integer may be a film, sheet or membrane, often of the same type, and of the same (generally uniform) thickness, as those used in conventional two-phase system, such as a dialysis unit for systemic therapy.

The film, sheet or membrane may be substantially flat, and depending on any pressure differential across it may require other materials on or in it to stiffen, reinforce or otherwise strengthen it.

However, this may not provide a system with sufficient functional surface area to remove materials deleterious to wound healing from wound exudate at a practical rate.

The surface area of any such film, sheet or membrane may be suitably be no less than $50\,mm^2$, such $100\,mm^2$ to $1\,m^2$, e.g. 500 to $25000\,mm^2$.

To be suitable for use, in particular in chronic wound dialysis, with relatively high concentrations of materials that are deleterious to wound healing, it may therefore be advantageous to provide a system in which the film, sheet or membrane of a polymeric material is in a more convoluted form.

This may be in the form of elongate structures, such as pipes, tubes hollow fibres or filaments or tubules of a round cross-section, e.g. elliptical or circular, e.g. in a parallel array with spaces therebetween.

The wound irrigant and/or wound exudate may recirculate through the inside and the cleansing fluid may pass into the spaces between adjacent pipes, tubes or tubules in a co- or preferably counter-current direction, or vice versa.

Again, materials deleterious to wound healing are removed into the dialysate, and the cleansed fluid, still containing materials that are beneficial in promoting wound healing, is returned via the recirculation tube to the wound.

Where the means for fluid cleansing is a two-phase system, e.g. in the form of a dialysis unit, or a biphasic extraction unit, the circulating fluid from the wound and the fluid reservoir passes across one surfaces of a significantly two-dimensional integer, for example a polymer film, sheet or membrane which is selectively permeable to materials deleterious to wound healing.

These are removed by passing a cleansing fluid across the other surface of the integer. The integer may be a film, sheet or membrane that is selectively permeable to the foregoing materials deleterious to wound healing.

These as above include oxidants, such as free radicals, e.g. peroxide and superoxide; iron II and iron III; all involved in oxidative stress on the wound bed;

proteases, such as serine proteases, e.g. elastase, trypsin; chymotrypsin and thrombin; cysteine protease inhibitors; matrix metalloproteases, e.g. collagenase; and carboxyl (acid) proteases;

endotoxins, such as lipopolysaccharides;

redox-sensitive genes that are deleterious to wound healing;

autoinducer signalling molecules, such as homoserine lactone derivatives, e.g. oxo-alkyl derivatives;

inhibitors of angiogenesis such as thrombospondin-1 (TSP-1), plasminogen activator inhibitor, or angiostatin (plasminogen fragment)

pro-inflammatory cytokines such as tumour necrosis factor alpha (TNFα) and interleukin 1 beta (IL-1β); and inflammatories, such as lipopolysaccharides, and e.g. histamine.

Examples of suitable materials for the film, sheet or membrane (typically in the form of conformable hollow bodies defined by the film, sheet or membrane, such as the structures described hereinbefore) include natural and synthetic polymeric materials.

The membrane may be of one or more hydrophilic polymeric materials, such as a cellulose derivative, e.g. regenerated cellulose, a cellulose mono-, di- or tri-esters, such as cellulose mono-, di- or tri-acetate, benzyl cellulose and Hemophan, and mixtures thereof.

Examples of other materials include hydrophobic materials, such as aromatic polysulphones, polyethersulphones, polyetherether-sulphones, polyketones, polyetherketones and polyetherether-ketones, and sulphonated derivatives thereof, and mixtures thereof.

Examples of other materials include hydrophobic materials, such as polyesters, such as polycarbonates and polyamides, e.g. Nylon 6-6 and 6-10; polyacrylates, including, e.g. poly(methyl methacrylate), polyacrylonitrile and copolymers thereof, for example acrylonitrile-sodium metallosulphonate copolymers; and poly(vinylidene chloride).

Suitable materials for the present membranes include thermoplastic polyolefins, such as polyethylene e.g. high-density polyethylene, polypropylene, copolymers thereof, for example with vinyl acetate and polyvinyl alcohol, and mixtures thereof.

The dialysis membrane should have a molecular weight cut off (MWCO) chosen to allow selective perfusion of species deleterious to wound healing that have been targeted for removal from the wound. For example, perfusion of the serine protease elastase (molecular weight 25900 Dalton) would require a membrane with MWCO>25900 Dalton. The MWCO threshold can be varied to suit each application between 1 and 3000000 Dalton.

Preferably, the MWCO should be as close as possible to this weight to exclude interference by larger competitor species.

For example, such a membrane with MWCO>25900 Dalton does not allow any significant amounts of the antagonist to elastase, alpha-1-antitrypsin (AAT) (molecular weight 54000 Dalton), which occurs naturally in wounds, to diffuse freely out of the wound fluid into the dialysate. The inhibitor, which is beneficial in promoting chronic wound healing, remains in contact with the wound bed, and can act beneficially on it, whilst the elastase that is deleterious to wound healing is removed.

Such use of the present apparatus is, e.g. favourable to the wound healing process in chronic wounds, such as diabetic foot ulcers, and especially decubitus pressure ulcers.

As noted hereinafter, antagonists, for example degrading enzymes, or sequestrating agents for elastase on the dialysate side of the membrane, may be used to enhance the removal of this protease from wound exudate.

Where it is desired to remove several different materials that are deleterious to wound healing, it may be advantageous to provide a system of modules in series, each of which removes a different material.

This allows incompatible cleansing materials to be used on the same fluid and/or wound exudates.

Preferably any such system is a conventional automated, programmable system which can cleanse the wound irrigant and/or wound exudate with minimal supervision.

As noted above in more detail, fluid passes from a cleansing fluid through a selectively permeable integer.

This may be the typical permeable polymer film, sheet or membrane of a two-phase system, such as a dialysis unit.

Additionally, solutes or disperse phase species will pass from the dialysate into the irrigant and/or wound exudate through the dialysis polymer film, sheet or membrane.

This property may be used to perfuse materials beneficial to wound healing into the irrigant and/or exudate from a dialysate.

In this less conventional type of infusion feed, a broad spectrum of species will usually pass into the exudate and/or irrigant fluid from the dialysate.

These include ionic species, such as bicarbonate;

vitamins, such as ascorbic acid (vitamin C) and vitamin E, and stable derivatives thereof, and mixtures thereof; to relieve oxidative stress on the wound bed;

pH buffering agents, such as potassium dihydrogen phosphate/disodium hydrogen phosphate, local analgesics/anaesthetics, such as lidocaine/lignocaine hydrochloride and xylocaine (adrenaline lidocaine) and/or anti-inflammatories, to reduce wound pain or inflammation or pain associated with the dressing nutrients to aid proliferation of wound cells, such as amino acids, sugars, low molecular weight tissue building blocks and trace elements; and other cell culture medium species; and gases, such as air, nitrogen, oxygen and/or nitric oxide.

For the purposes of fluid cleansing in the apparatus of the present invention, both the single-phase system, such as an ultrafiltration unit, and two-phase system, such as a dialysis unit, may have captive (non-labile, insoluble and/or immobilised) species such as the following.

These are bound to an insoluble and/or immobilised) substrate over and/or through which the irrigant and/or wound exudate from, the wound dressing passes in turn to the fluid recirculation tube(s):

antioxidants and free radical scavengers, such as 3-hydroxytyramine (dopamine), ascorbic acid (vitamin C), vitamin E and glutathione, and stable derivatives thereof, and mixtures thereof; to relieve oxidative stress on the wound bed;

metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine); iron III reductants;

protease inhibitors, such as TIMPs and alpha 1-antitrypsin (AAT); serine protease inhibitors, such as 4-(2-aminoethyl)-benzene sulphonyl fluoride (AEBSF, PefaBloc) and Nα-p-tosyl-L-lysine chloro-methyl ketone (TLCK) and ε-aminocaproyl-p-chlorobenzylamide; cysteine protease inhibitors; matrix metalloprotease inhibitors; and carboxyl (acid) protease inhibitors;

sacrificial redox materials that are potentially or actually beneficial in promoting wound healing, by the removal of materials that trigger the expression into wound exudate of redox-sensitive genes that are deleterious to wound healing; autoinducer signalling molecule degraders, which may be enzymes; and anti-inflammatory materials to bind or destroy lipopolysaccharides, e.g. peptidomimetics Other physiologically active components of the exudate that are deleterious to wound healing may be removed in this way.

These may be removed with suitable chelators and/or ion exchangers, degraders, which may be enzymes, or other species.

The following types of functionalised substrate has sites on its surface that are capable of removing materials deleterious to wound healing on passing the circulating fluid from the wound and the fluid reservoir over them:

heterogeneous resins, for example silica-supported reagents such as: metal scavengers,
3-(diethylenetriamino)propyl-functionalised silica gel
2-(4-(ethylenediamino)benzene)ethyl-functionalised silica gel
3-(mercapto)propyl-functionalised silica gel
3-(1-thioureido)propyl-functionalised silica gel
triamine tetraacetate-functionalised silica gel or electrophilic scavengers,
4-carboxybutyl-functionalised silica gel
4-ethyl benzenesulfonyl chloride-functionalised silica gel
propionyl chloride-functionalised silica gel
3-(isocyano)propyl-functionalised silica gel
3-(thiocyano)propyl-functionalised silica gel
3-(2-succinic anhydride)propyl-functionalised silica gel
3-(maleimido)propyl-functionalised silica gel or nucleophilic scavengers,
3-aminopropyl-functionalised silica gel
3-(ethylenediamino)-functionalised silica gel
2-(4-(ethylenediamino)propyl-functionalised silica gel
3-(diethylenetriamino)propyl-functionalised silica gel
4-ethyl-benzenesulfonamide-functionalised silica gel
2-(4-toluenesulfonyl hydrazino)ethyl-functionalised silica gel
3-(mercapto)propyl-functionalised silica gel
dimethylsiloxy-functionalised silica gel or base or acid scavengers,
3-(dimethylamino)propyl-functionalised silica gel
3-(1,3,4,6,7,8-hexahydro-2H-pyrimido-[1,2-α]pyrimidino) propyl-functionalised silica gel
3-(1-imidazol-1-yl)propyl-functionalised silica gel
3-(1-morpholino)propyl-functionalised silica gel
3-(1-piperazino)propyl-functionalised silica gel
3-(1-piperidino)propyl-functionalised silica gel
3-(4,4'-trimethyldipiperidino)propyl-functionalised silica gel
2-(2-pyridyl)ethyl-functionalised silica gel
3-(trimethylammonium)propyl-functionalised silica gel or the reagents,
3-(1-cyclohexylcarbodiimido)propyl-functionalised silica gel
TEMPO-functionalised silica gel
2-(diphenylphosphino)ethyl-functionalised silica gel
2-(3,4-cyclohexyldiol)propyl-functionalised silica gel
3-(glycidoxy)propyl-functionalised silica gel
2-(3,4-epoxycyclohexyl)propyl-functionalised silica gel
1-(allyl)methyl-functionalised silica gel
4-bromopropyl-functionalised silica gel
4-bromophenyl-functionalised silica gel
3-chloropropyl-functionalised silica gel
4-benzyl chloride-functionalised silica gel
2-(carbomethoxy)propyl-functionalised silica gel
3-(4-nitrobenzamido)propyl-functionalised silica gel
3-(ureido)propyl-functionalised silica gel or any combinations of the above.

The use of such captive (non-labile, insoluble and/or immobilised) species, such as the foregoing, bound to an insoluble and immobilised) substrate over and/or through which the irrigant and/or wound exudate from, the wound dressing passes has been described hereinbefore as suitable for the means for fluid cleansing.

However, they may additionally, where appropriate, be used in any part of the apparatus that is in contact with the irrigant and/or wound exudate, but often within the dressing, for removal of materials deleterious to wound healing from wound.

A backing layer in the wound dressing with ribs or ridges may be used to assist in channelling fluid across a larger area over a longer dwell time, and hence improve the cleansing of the irrigant in the wound dressing.

The means for fluid cleansing may additionally, where appropriate, comprise one or more macroscopic and/or microscopic filters.

These are to retain particulates, e.g. cell debris and microorganisms, allowing proteins and nutrients to pass through.

Alternatively, a less conventional type of two-phase system (see above), such as a dialysis unit, may be used as the means for fluid cleansing. In this type, the dialysis polymer film, sheet or membrane is not an integer selectively permeable to materials deleterious to wound healing, such as proteases, such as serine proteases, e.g. elastase, trypsin; chymotrypsin and thrombin; cysteine protease inhibitors; matrix metalloproteases, e.g. collagenase; and carboxyl (acid) proteases;

endotoxins, such as lipopolysaccharides;

inhibitors of angiogenesis such as thrombospondin-1 (TSP-1), plasminogen activator inhibitor, or angiostatin (plasminogen fragment);

pro-inflammatory cytokines such as tumour necrosis factor alpha (TNFα) and interleukin 1 beta (IL-1β); and oxidants, such as free radicals, e.g., e.g. peroxide and superoxide; metal ions, e.g. iron II and iron III; all involved in oxidative stress on the wound bed.

It will however also permit components of the exudate from a wound and/or irrigant fluid that may be larger or smaller molecules, but are beneficially involved in wound healing to pass into and through it.

In the dialysate, or preferably in one or more solid structural integers with at least one surface in contact with the dialysate, in the means for fluid cleansing, there are one or more materials that can remove materials deleterious to wound healing from wound exudate, by being antagonists to such species, for example enzymes or others, such as protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide; cysteine protease inhibitors; matrix metalloprotease inhibitors; and carboxyl (acid) protease inhibitors;

peroxide inhibitors, such as catalase;

binders and/or degraders, such as anti-inflammatory materials to bind or destroy lipopolysaccharides, e.g. peptidomimetics;

anti-oxidants, such as 3-hydroxytyramine (dopamine), ascorbic acid (vitamin C), vitamin E and glutathione, and stable derivatives thereof, and mixtures thereof; to relieve oxidative stress on the wound bed; and chelators and/or ion exchanges, such as desferrioxamine (DFO), 3-hydroxytyramine (dopamine).

They further include peptides (including cytokines, e.g. bacterial cytokines, such as α-amino-γ-butyrolactone and L-homocarnosine); and sacrificial redox materials that are potentially or actually beneficial in promoting wound healing, such as iron III reductants; and/or remove materials that trigger the expression into wound exudate of redox-sensitive genes, by degrading them; and other physiologically active components.

In use of the two-phase system dialysis unit, of this less conventional type, a broad spectrum of species will usually pass into the dialysate from the exudate.

Some (mainly ionic) species will pass from the dialysate into the irrigant and/or wound exudate through the dialysis polymer film, sheet or membrane that is not very selectively permeable to materials deleterious to wound healing.

The components of the exudate from a wound and/or irrigant fluid will diffuse freely to and fro through it.

If (preferably) none of the dialysate is voided to waste, e.g. to a collection bag, a steady state concentration equilibrium is eventually set up between the dialysate and the irrigant and/or wound exudate, which is 'topped up' from the wound dressing.

Circulating wound fluid aids in the quicker attainment of this equilibrium of materials beneficial in promoting wound healing.

It also returns them to the site where they can be potentially of most benefit, i.e. the wound bed.

The target materials deleterious to wound healing also pass into the dialysate from the exudate through the dialysis polymer film, sheet or membrane that is not very selectively permeable to materials deleterious to wound healing.

Unlike the other components of the exudate from a wound and/or irrigant fluid, the target materials deleterious to wound healing come into contact with the dialysate, or preferably with one or more solid structural integers with at least one surface in the dialysate, and are removed by the appropriate antagonists, binders and/or degraders, chelators and/or ion exchangers and redox agents, etc.

The cleansed fluid, still containing some materials that are beneficial in promoting wound healing, is returned to the recirculation tube.

Unlike the other components of the exudate from a wound and/or irrigant fluid the target materials are constantly removed from the dialysate, very little of these species will pass from the dialysate, into the irrigant and/or wound exudate, and a steady state concentration equilibrium is not set up, even if the species are constantly 'topped up' from the wound dressing.

It is believed that circulating wound fluid aids in removal from recirculation of the materials deleterious to wound healing from wound exudate, whilst retaining materials that are beneficial in promoting wound healing in contact with the wound.

A particular advantage of this form of the two-phase system is where a material that can remove materials deleterious to wound healing from wound exudate is (cyto)toxic or bioincompatible, or not inert to any components that are beneficial in promoting wound healing.

The system does not allow any significant amounts of antagonist to diffuse freely out of the dialysate into the irrigant fluid. The active material can act beneficially on the fluid however.

The film sheet or membrane is preferably a dialysis membrane of molecular weight cut off (MWCO) chosen to allow perfusion of species targeted for sequestration or destruction.

For example, sequestration of the serine protease elastase (molecular weight 25900 Dalton) would require a membrane with MWCO>25900 Dalton.

The MWCO threshold can be varied to suit each application between 1 and 3000000 Dalton. Preferably, the MWCO should be as close as possible to this weight to exclude sequestering interference by larger competitor species.

Both the single-phase system, such as an ultrafiltration unit, and two-phase system, such as a dialysis unit, may be in modular form that is relatively easily demountable from the apparatus of the invention. The system may suitably comprise one or more such modules.

The conduits through which respectively
a) the irrigant and/or wound exudate passes from the wound dressing and
b) the cleansed fluid, still containing materials that are beneficial in promoting wound healing, is returned to the recirculation tube, and
c) (in the case where the means is provided in the form of a two-phase system, such as an dialysis unit) through which the cleansing fluid enters and exits the means preferably have means for, on module disconnection and withdrawal,
i) switching off the flow and
ii) providing an immediate fluid-tight seal or closure over the ends of the conduits and the cooperating tubes in the rest of the apparatus of the invention so exposed, to prevent continuing passage of irrigant and/or exudate and cleansed fluid, and cleansing fluid.

The apparatus of the invention for irrigating, supplying thermal energy to and/or cleansing wounds is provided with means for bleeding the offtake and/or recirculation tubes, such as a regulator, such as a valve or other control device for bleeding fluids from the wound.

The device for moving fluid through the wound and means for fluid cleansing is used to move irrigant to the wound dressing and apply the desired positive or negative pressure on the wound bed.

The desired balance of fluid in recirculation tube will typically be regulated by means of
a) the means for bleeding the offtake and/or recirculation tubes,
b) the means for flow switching between supply and recirculation, and/or
c) the means for moving fluid over the wound bed and through the means for fluid cleansing, as appropriate.
Thus, e.g. if
a) the apparatus for irrigating, supplying thermal energy to and/or cleansing wounds is a single-phase system, such as an ultrafiltration unit,
b) the wound is not in a highly exuding state and c) it is not appropriate or desired to admit fluid into the wound from the fluid reservoir, there is no or negligible change in the balance of fluid in recirculation.

Once it has been primed throughout, e.g. to the desired positive or negative pressure on the wound bed, the apparatus may be operated as a closed recirculating system.

The means for flow switching between supply and recirculation tubes is set to close the wound to the fluid reservoir via the fluid supply tube, and the means for bleeding the offtake and/or recirculation tubes are also closed.

If a) the apparatus for irrigating, supplying thermal energy to and/or cleansing wounds is a single-phase system, such as an ultrafiltration unit,
b) the wound is in a highly exuding state and/or
c) it is appropriate or desired to admit fluid into the wound from the fluid reservoir, there is a positive change in the balance of fluid in recirculation.

Once it has been primed throughout, e.g. to the desired positive or negative pressure on the wound bed, the apparatus cannot be operated as a closed recirculating system, without the pressure to the wound bed increasing, possibly undesirably.

The means for bleeding the offtake and/or recirculation tubes must be opened to some extent to relieve positive pressure on the wound bed. The bleed-off may be voided to waste, e.g. to a collection bag.

Materials that are beneficial in promoting wound healing may be lost to the site where they can be potentially of most benefit, i.e. the wound bed, when the therapy is applied in this way.

However, the balance of fluid in recirculation may be routinely adjusted to minimise this undesired loss.

The factors that determine the balance of fluid in recirculation in an apparatus with a two-phase system means for fluid cleansing in the form of a dialysis unit, or a biphasic extraction unit have been described in detail hereinbefore in connection with the operation of the apparatus. It is sufficient to note here that at some point after steady state recirculation established through the length of the apparatus flow path, it may be necessary that any bleed valve is opened, if overall the fluid level is increasing by transfer from the dialysate to an undesirable extent.

Other combinations, and the necessary adjustments to maintain the desired balance of fluid in recirculation tube by means of a) the means for bleeding the offtake and/or recirculation tubes,
b) the means for flow switching between supply and recirculation, and/or
c) the means for moving fluid will be apparent to the skilled person.

The outlet from the means for bleeding the offtake and/or recirculation tubes may be collected and monitored and used to diagnose the status of the wound and/or its exudate.

The waste reservoir may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the waste reservoir will be largely determined by its function. To be suitable for use, the material need only be fluid-impermeable once in use, and flexible.

Examples of suitable materials for the fluid reservoir include synthetic polymeric materials, such as polyolefins, such as poly (vinylidene chloride).

Suitable materials for the present purpose also include polyethylene, e.g. high-density polyethylene, polypropylene, copolymers thereof, for example with vinyl acetate and mixtures thereof.

In a second aspect of the present invention there is provided a conformable wound dressing, characterised in that it comprises a backing layer with a wound-facing face which is capable of forming a relatively fluid-tight seal or closure over a wound and has at least one inlet pipe for connection to a fluid supply tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure over the wound, the dressing having means for supplying thermal energy to the fluid in the wound.

The dressing is advantageously provided for use in a bacteria-proof pouch. Examples of suitable forms of such wound dressings are as described by way of example hereinbefore.

It is an object of the present invention
a) obviate at least some of the disadvantages of known aspiration and/or irrigation therapies, and
b) provide a system of therapy which
 i) can remove materials deleterious to wound healing from wound exudate, whilst retaining materials that are beneficial in promoting wound healing in contact with the wound bed, and/or
 ii) which allows fluids containing active amounts of materials that are beneficial in promoting wound healing to pass into and/or through the wound in contact with the wound bed.

Thus, in a third aspect of the present invention there is provided a method of treating wounds to promote wound healing using the apparatus for irrigating, supplying thermal energy to and/or cleansing wounds of the present invention.

The present invention will now be described by way of example only with reference to the accompanying drawings in which:

FIG. 1 is a schematic view of an apparatus for irrigating, supplying thermal energy to and/or cleansing a wound according to the first aspect of the present invention.

It has a single-phase system means for fluid cleansing in the form of an ultrafiltration unit.

FIG. 2 is a schematic view of an apparatus for irrigating, supplying thermal energy to and/or cleansing a wound according to the first aspect of the present invention.

It has a two-phase system means for fluid cleansing in the form of a dialysis unit, or a biphasic extraction unit.

The means for supplying conducted thermal energy are omitted from the schematics for clarity.

Figure 1:
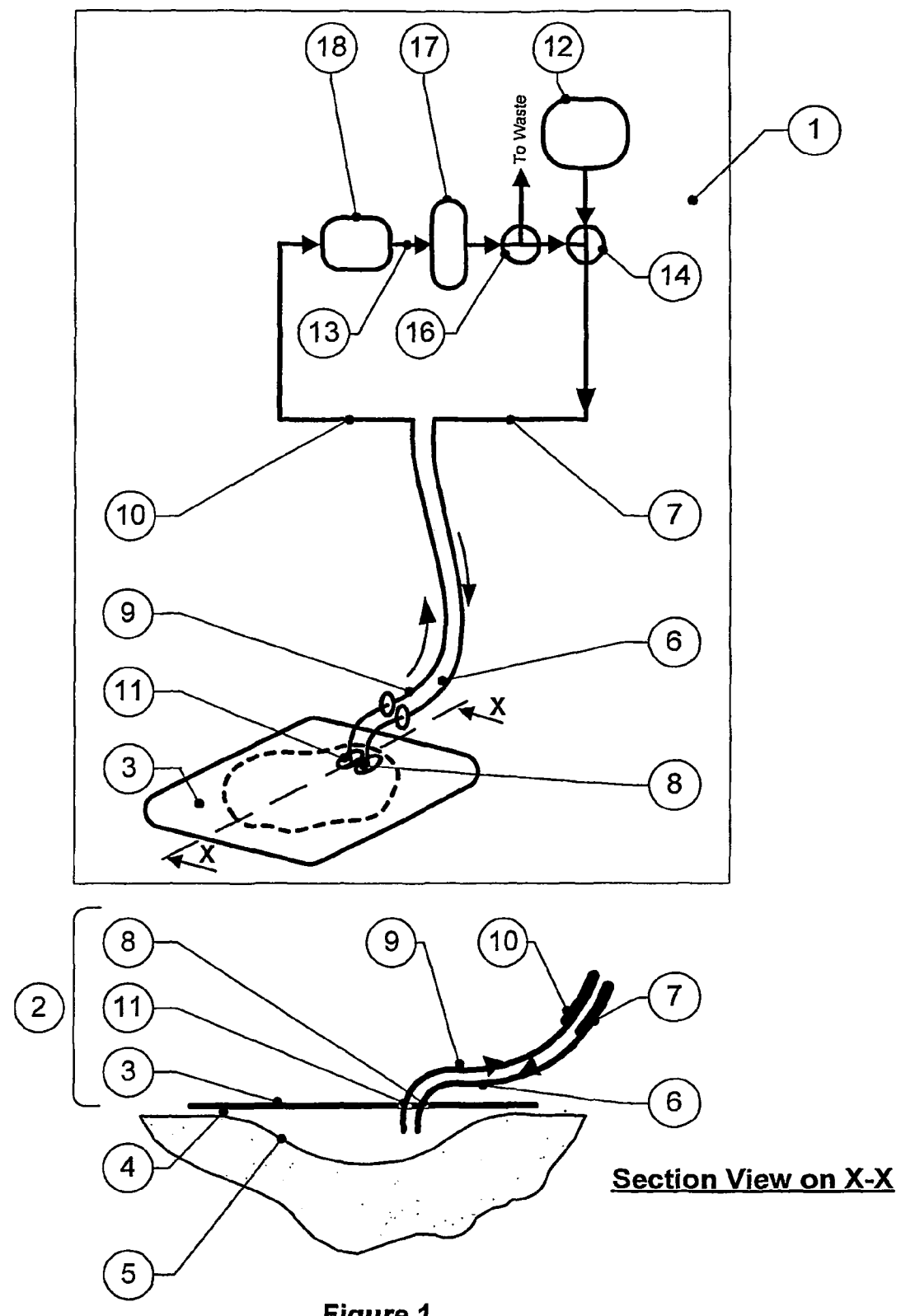

Referring to FIG. 1, the apparatus (1) for irrigating, supplying thermal energy to and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (5) at (8), and one outlet pipe (9) for connection to a fluid offtake tube (10), which passes through the wound-facing face at (11), the points (8), (11) at which the inlet pipe and the outlet pipe passes through and/or under the wound-facing face forming a relatively fluid-tight seal or closure over the wound, and means for supplying conducted thermal energy to the fluid in the wound in the form of an electrical heater (111) (not shown) on the inlet pipe (6). (In a variant of this apparatus noted further below, the means for supplying conducted thermal energy to the fluid in the wound is in the form of an electrical heat pad mounted on top of the backing layer (3) which is capable of conducting heat to the wound (5) through the irrigant.), the inlet pipe being connected via means for flow switching between supply and recirculation, here a T-valve (14), by the fluid supply tube (7) to a fluid reservoir (12) and to a fluid recirculation tube (13) having a means for bleeding the tube, here a bleed T-valve (16) to waste, e.g. to a collection bag (not shown), the outlet pipe (9) being connected to a fluid offtake tube (15), connected in turn to means for fluid cleansing (17), here in the form of an ultrafiltration unit, connected to the inlet pipe (6) via the fluid recirculation tube (13) and T-valve (14), and a device for moving fluid through the wound and means for fluid cleansing (17), here a peristaltic pump (18), e.g. preferably a small portable peristaltic pump, acting on the fluid circulation tube (13) with the peripheral rollers on its rotor (not shown) to apply a low negative pressure on the wound. The ultrafiltration unit (17) is a single-phase system.

In this the circulating fluid from the wound and the fluid reservoir passes through a self-contained system in which materials deleterious to wound healing are removed and the cleansed fluid, still containing materials that are beneficial in promoting wound healing, is returned via the recirculation tube to the wound bed.

(In a variant of this apparatus, there are two inlet pipes (6), which are connected respectively to a fluid supply tube (7) and fluid recirculation tube (13), respectively having a first valve (19) for admitting fluid into the wound from the fluid reservoir (12) and a second valve (20) for admitting fluid into the wound from the recirculation tube. Usually in use of the apparatus, when the first valve (19) is open, the second valve (20) is shut, and vice versa.)

In use of the apparatus (1), the valve (16) is opened to a collection bag (not shown), and the T-valve (14) is turned to admit fluid from the fluid reservoir to the wound dressing through the fluid supply tube (7) and inlet pipe (6).

(In the variant of this apparatus having two inlet pipes (6), which are connected respectively to a fluid supply tube (7) and fluid recirculation tube (13), the first valve (19) for admitting fluid into the wound from the fluid reservoir (12) is opened and the second valve (20) is shut, and vice versa.)

The pump (18) is started to nip the fluid recirculation tube (13) with the peripheral rollers on its rotor (not shown) to apply a low positive pressure on the wound. It is allowed to run until the apparatus is primed throughout the whole length of the apparatus flow path and excess fluid is voided to waste via the bleed T-valve (16) into the collection bag (not shown).

The electrical heater (111) on inlet pipe (6) is turned on to supply conducted thermal energy to the fluid in the wound.

The T-valve (14) is then turned to switch from supply and recirculation, i.e. is set to close the wound to the fluid reservoir (12) but to admit fluid into the wound from the fluid recirculation tube (13), and the bleed T-valve (16) is simultaneously closed.

(In the variant of this apparatus, where there are two inlet pipes (6), which are connected respectively to a fluid supply tube (7) and fluid recirculation tube (13), the first valve (19) is closed and a recirculating system set up by opening the second valve (20) for admitting fluid into the wound from the recirculation tube (13).

The circulating fluid from the wound and the fluid reservoir (12) passes through the ultrafiltration unit (17). Materials deleterious to wound healing are removed and the cleansed fluid still containing materials that are beneficial in promoting wound healing, is returned via the recirculation tube (13) to the wound bed.

The recirculation of fluid may be continued as long as desired.

Switching between supply and recirculation is then reversed, by turning the T-valve (14) to admit fluid from the fluid reservoir to the wound dressing through the fluid supply tube (7) and inlet pipe (6).

(In the variant of this apparatus having two inlet pipes (6), which are connected respectively to a fluid supply tube (7) and fluid recirculation tube (13), the first valve (19) for admitting fluid into the wound from the fluid reservoir (12) is opened and the second valve (20) is shut, and vice versa.)

The bleed valve (16) is simultaneously opened, so that fresh fluid flushes the recirculating system.

The running of the pump (18) may be continued until the apparatus is flushed, when it and the fluid recirculation is stopped, and the electrical heater (111) on inlet pipe (6) is turned off.

If, e.g. the wound is in a highly exuding state, there is a positive change in the balance of fluid in recirculation. It may be necessary to bleed fluid from recirculation, by opening the bleed T-valve (16) to bleed fluid from the recirculation tube (13).

Figure 2:
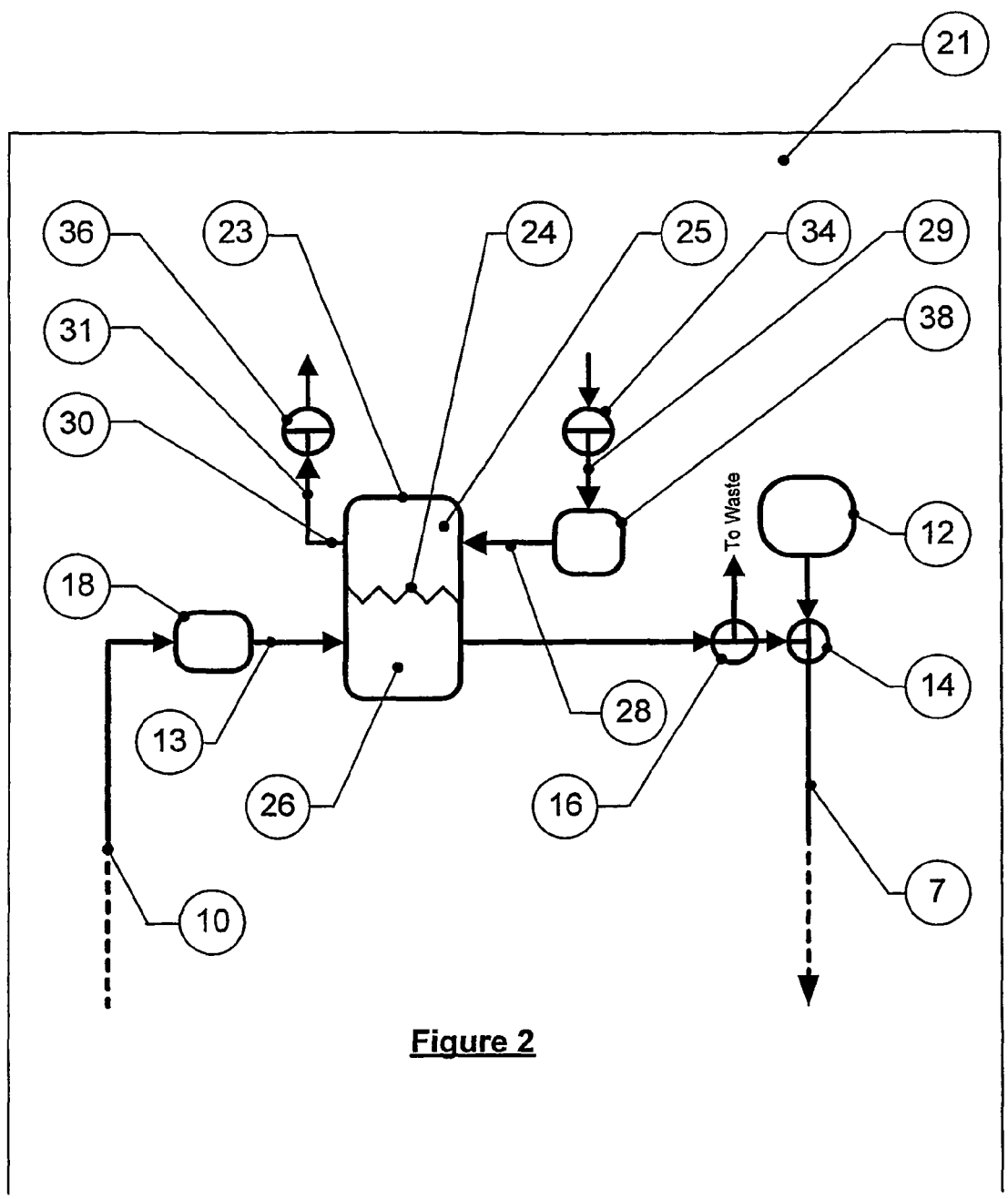

Referring to FIG. 2, the apparatus (21) is a variant of that of FIG. 1, with identical, and identically numbered, components, except for the means for fluid cleansing, which is in the form of a two-phase system, here a dialysis unit (23).

In this, there is one system through which the circulating fluid from the wound and the fluid reservoir passes and from which deleterious materials are removed by selectively permeable contact with a second system, through which passes a cleansing fluid.

The dialysis unit (23) thus has an internal polymer film, sheet or membrane (24), selectively permeable to materials deleterious to wound healing, which divides it into a) a first chamber (25), through which passes a cleansing fluid across one surface of the polymer film, sheet or membrane, and b) a second chamber (26), through which passes the circulating fluid from the wound and the fluid reservoir (12), and from which deleterious materials are removed The dialysis unit (23) thus has a dialysate inlet pipe (28) connecting to a dialysate supply tube (29) which passes to a peristaltic pump (38), e.g. preferably a small portable peristaltic pump, acting on the dialysate supply tube (29) with the peripheral rollers on its rotor (not shown) to supply cleansing fluid across the surface of the polymer film, sheet or membrane (28) in the first chamber (25) from a dialysate reservoir (not shown) via a valve (34).

The dialysis unit (23) also has a dialysate outlet pipe (30) connecting to a dialysate outlet tube (31) which passes to waste via a second bleed T-valve (36) into, e.g. a collection bag (not shown).

Operation of this apparatus is similar to that of FIG. 1, except for the dialysis unit (23), in that at some point after the irrigation system is primed and steady state recirculation established through the length of the apparatus flow path, the valve (34) and second bleed valve (36) are opened.

The pump (38) is started to nip fluid dialysate tube (29) with the peripheral rollers on its rotor (not shown) to pump cleansing fluid to the first chamber from a dialysate reservoir (not shown) and out to waste via the bleed valve (36) into the collection bag (not shown).

The dialysis unit (23) is a module (or scrubbing cartridge) with a substrate that changes colour to indicate the presence of detrimental factors in the cleansed fluid, and that the scrubbing cartridge is exhausted and should be renewed.

Referring to FIGS. 3 to 7, each dressing (41) is in the form of a conformable body defined by a microbe-impermeable film backing layer (42) with a uniform thickness of 25 micron, with a wound-facing face (43) which is capable of forming a relatively fluid-tight seal or closure over a wound.

The backing layer (42) extends in use on a wound over the skin around the wound. On the proximal face of the backing layer (43) on the overlap (44), it bears an adhesive film (45), to attach it to the skin sufficiently to hold the wound dressing in place in a fluid-tight seal around the periphery of the wound-facing face (43) of the wound dressing.

Figure 3:
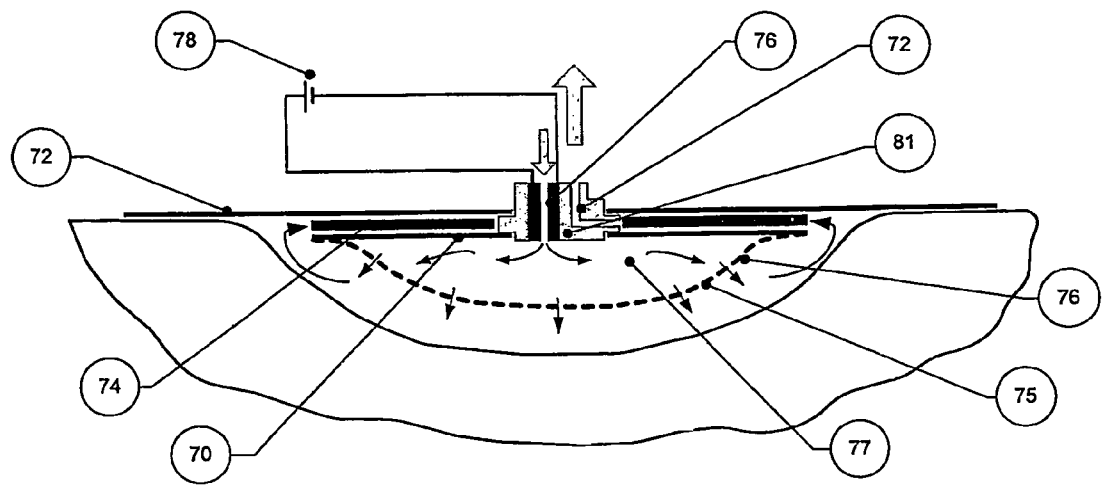
FIGS. 3 to 6 are cross-sectional side views of conformable wound dressings, of the second aspect of the present invention for aspirating and/or irrigating wounds.

There is one inlet pipe (46) for connection to a fluid supply tube (not shown), which passes through and/or under the wound-facing face (43), and one outlet pipe (47) for connection to a fluid offtake tube (not shown), which passes through and/or under the wound-facing face (43), Referring to FIG. 3, one form of the dressing comprises a circular sheet (70) that lies under a circular backing layer (72) and is permanently attached to a boss (81), which is e.g. heat-sealed to the backing layer (72).

An annular layer of foam (74) formed of a suitable material, e.g. a resilient thermoplastic, preferably a reticulated filtration polyurethane foam with small apertures or pores, spaces the sheet (70) from the backing layer and surrounds the boss (81).

A downwardly dished membrane (75) with openings (76) is permanently attached to the sheet (70) by heat-sealing to form a chamber (77) with the sheet (70).

An inlet pipe (76) and outlet pipe (77) are mounted centrally in the boss (81) and pass through the backing layer (72).

The inlet pipe (76) is made of a polyurethane tubular core (not shown) surrounded by an annulus of resistive conductive material, such as one of the resistive alloys noted hereinbefore, which generates thermal energy when a voltage drop is applied over it. It is connected to a cell (78), shown schematically, which applies a voltage drop over it.

The inlet pipe (76) communicates with the interior of the chamber (77), which thus forms an inlet manifold that distributes heated fluid directly to the wound when the dressing is in use.

The outlet pipe (77) extends radially immediately under the backing layer (3) and communicates with the inner face of the layer of foam (74), which forms an outlet manifold.

This form of the dressing is a more suitable layout for shallow wounds

Figure 4:
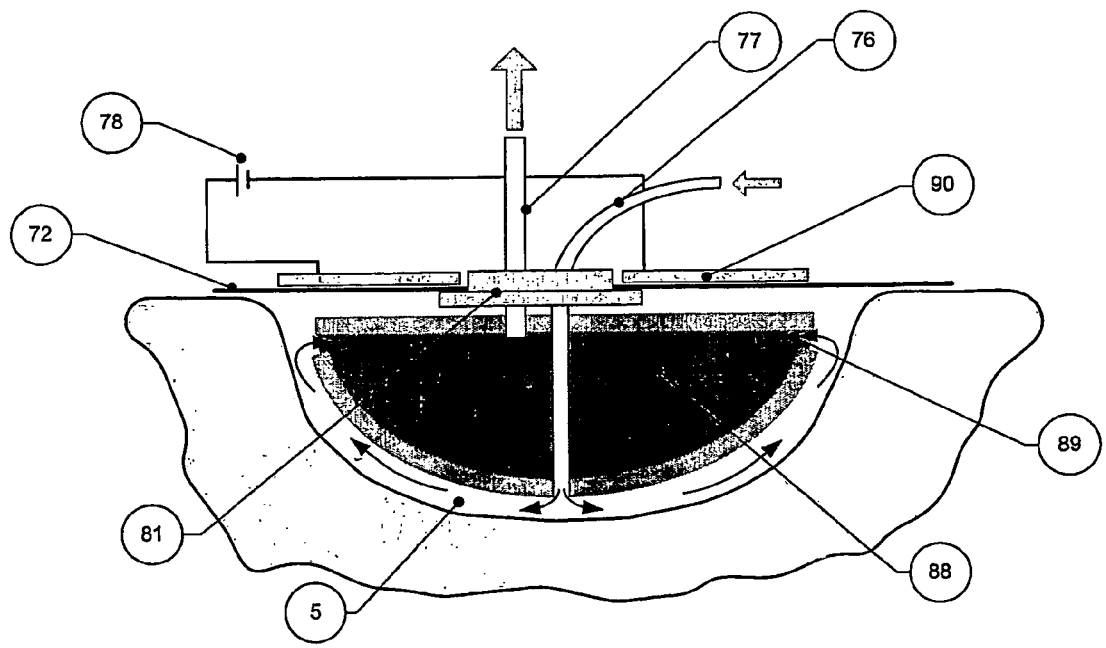

Another form of dressing is shown in FIG. 4. An inlet pipe (76) and outlet pipe (77) are mounted centrally in a boss (81) in, and pass through a backing layer (3). An oblately hemispheroidal filler (88) with an annular groove (89) may be permanently attached to the pipes (76) and (77). It is formed of a suitable material, e.g. a resilient thermoplastic foam, preferably a reticulated filtration polyurethane foams with small apertures or pores.

An annular electrical heat pad (90) is mounted around the boss (81) on top of the backing layer (3), which is capable of conducting heat to the wound (5) through the irrigant.

It may be in the form of non-woven or woven fabric, such as a woven layer or sheet of carbon fibres or a fabric, such as a woven layer or sheet made essentially of carbonised acrylate, such as polyacrylonitrile and copolymers thereof, which generate thermal energy when a voltage drop is applied over it.

Alternatively, it may be an electrically insulating flat sheet or membrane substrate that has an electrically resistive but conductive printed circuit on it. It is connected to a cell (78), shown schematically, which applies a voltage drop over it.

The inlet pipe (76) communicates with the wound space at the lowest point of the filler (88). The outlet pipe (77) communicates with the groove (89), and effectively collects the fluid from the wound periphery when the dressing is in use.

This form of the dressing is a more suitable layout for deeper wounds.

Figure 5:
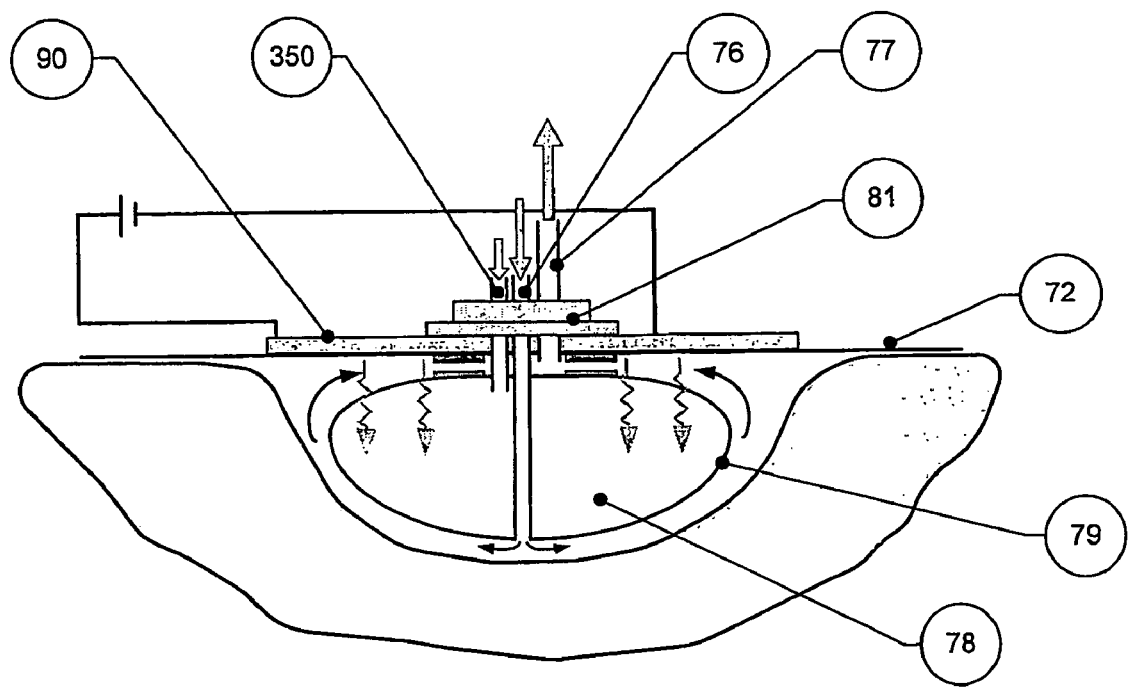

In FIG. 5, an inlet pipe (76) and outlet pipe (77) are mounted centrally in a boss (81) in, and pass through a backing layer (3).

An oblately spheroidal conformable hollow body (78) is defined by a membrane (79) which is filled with a fluid, here air or nitrogen, that urges it to the wound shape, and is permanently attached to the pipes (76) and (77). It is formed of a suitable material, e.g. a resilient thermoplastic, preferably a reticulated filtration polyurethane foam with small apertures or pores.

The inflation inlet pipe (350) communicates with the interior of the hollow body (78), to permit inflation of the body (78). The inlet pipe (76) extends through the hollow body (78). The outlet pipe (77) communicates with an outlet manifold formed by a series of radial apertures in a foam disc (87) immediately under the backing layer, which collects the fluid from the wound periphery when the dressing is in use.

An electrical heater (90) is mounted under the boss (81) on top of the backing layer (3), which is transparent to radiant heat, and so permit its transmission to the wound (5) through the irrigant.

It may be in the form of a near infrared radiant heater that generates thermal energy when a voltage drop is applied over it. It is connected to a cell (78), shown schematically, which applies a voltage drop over it.

Figure 6A:
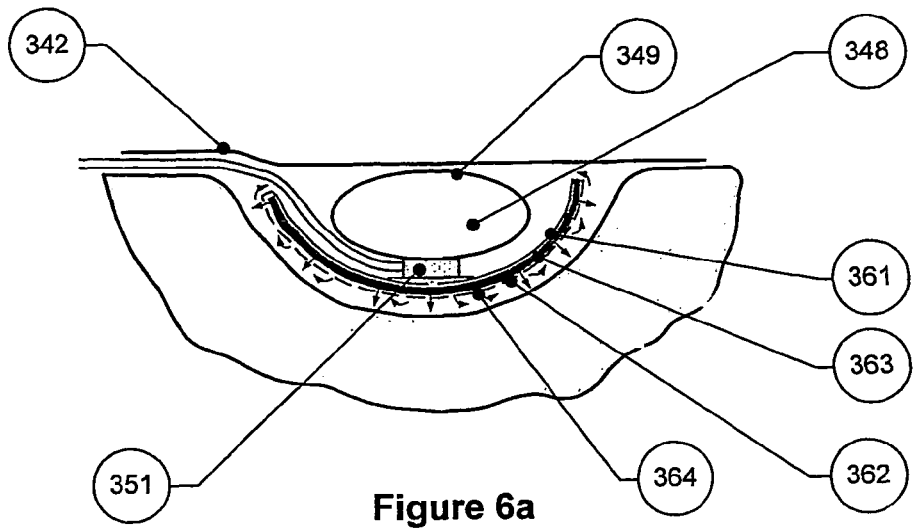

Referring to FIG. 6a, another form for deeper wounds is shown. This comprises a circular, or more usually square or rectangular, backing layer (342) and a chamber (363) in the form of a deeply indented disc much like a multiple Maltese cross or a stylised rose.

Figure 6B:
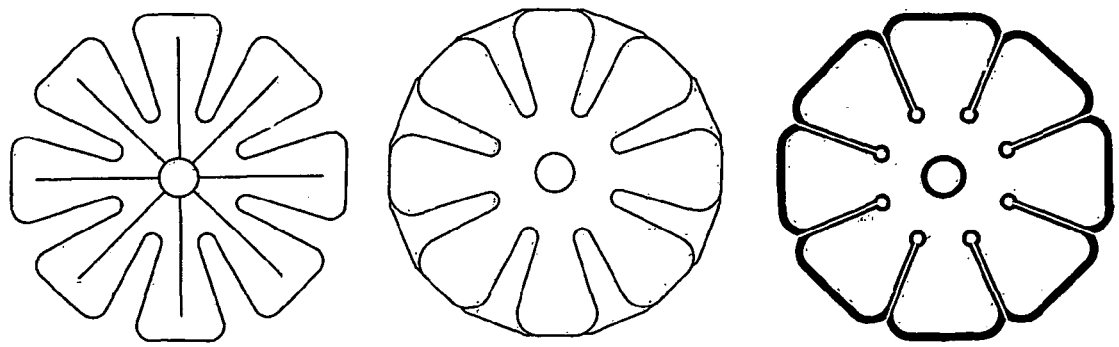
Figure 6B:
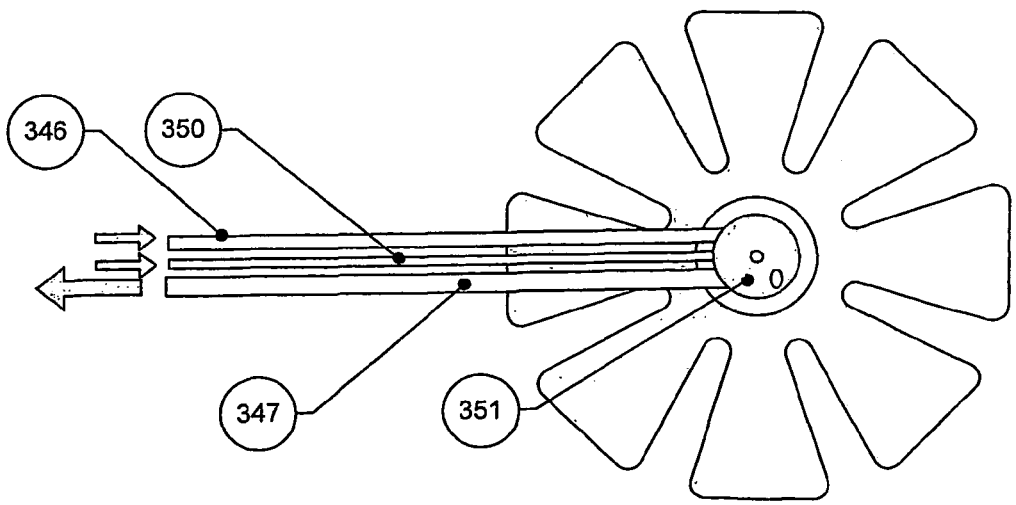

This is defined by an upper impervious membrane (361) and a lower porous film (362) with apertures (364) that deliver the irrigant fluid directly to the wound bed over an extended area, and thus effectively forms an inlet manifold. Three configurations of the chamber (363) are shown in FIG. 6b, all of which are able to conform well to the wound bed by the arms closing in and possibly overlapping in insertion into the wound.

The space above the chamber (363) is filled with a wound filler (348) under the backing layer (342).

This comprises an oblately spheroidal conformable hollow body, defined by a membrane (349) that is filled with a fluid, here air or nitrogen, that urges it to the wound shape.

A moulded hat-shaped boss (351) is mounted centrally on the upper impervious membrane (361) of the chamber (363). It has three internal channels, conduits or passages through it (not shown), each with entry and exit apertures.

The filler (348) is attached to the membrane (361) of the chamber (363) by adhesive, heat welding or a mechanical fixator, such as a cooperating pin and socket.

An inflation inlet pipe (350), inlet pipe (346) and outlet pipe (347) pass under the edge of the proximal face of the backing layer (342) of the dressing, and extend radially immediately under the filler (348) and over the membrane (361) of the chamber (363) to each mate with an entry aperture in the boss (351).

An exit to the internal channel, conduit or passage through it that receives the inflation inlet pipe (350) communicates with the interior of the hollow filler (348), to permit inflation.

An exit to the internal channel, conduit or passage that receives the inlet pipe (346) communicates with the interior of the chamber (363) to deliver the irrigant fluid via the chamber (363) to the wound bed over an extended area.

Similarly, an exit to the internal channel, conduit or passage that receives the outlet pipe (347) communicates with the space above the chamber (363) and under the wound filler (348), and collects flow of irrigant and/or wound exudate radially from the wound periphery.

At its distal end furthest from the wound), the inlet pipe (346) is permanently attached to, and communicate with the interior of, a recirculation tube (413) in the form of a spiral or loop or a more convoluted form. This is a meandering, tortuous or winding path (not shown) sandwiched between parallel electrically heated plates of resistive conductive material, such as a resistive alloys (also not shown), all within a moulded disc-shape housing case (416).

This has entry and exit apertures in the edge extending between the faces of the case, through which the irrigant tubing passes. The heated plates connected to a cell (419) shown schematically, which applies a voltage drop over them in use.

The boss (351) mounted centrally on the upper impervious membrane (361) of the chamber (363) may also include a lumen through it (not shown in the Figure) with entry and exit apertures. A fourth pipe may also pass under the edge of the proximal face of the backing layer (342) of the dressing, and extend radially immediately under the filler (348) and over the membrane (361) of the chamber (363) to mate with the lumen entry aperture in the boss (351).

An exit to the internal channel, conduit or passage through it that receives this pipe may communicate with the space above the chamber (363) and under the wound filler (348), to permit the monitoring of wound pressure.

Figure 7:
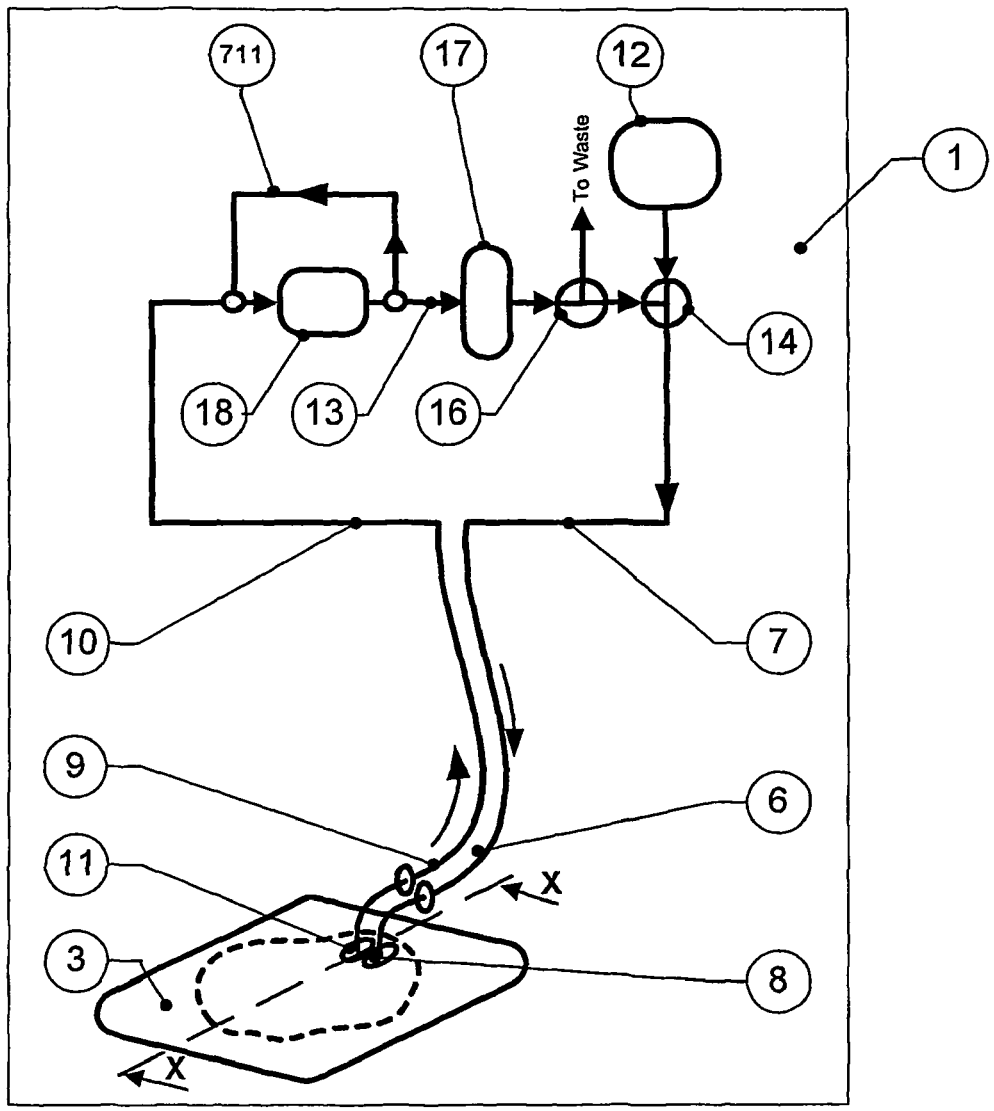
FIG. 7 is a schematic view of an apparatus for aspirating, irrigating and/or cleansing a wound according to the first aspect of the present invention. It has a single-phase system means for fluid cleansing in the form of an ultrafiltration unit.
Figure 7:
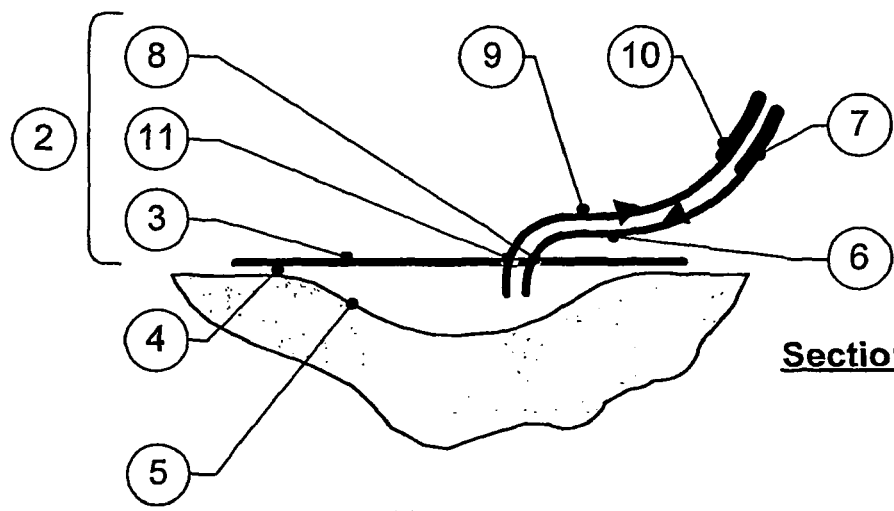

Referring to FIG. 7, the apparatus (1) for aspirating, irrigating and/or cleansing wounds is a variant of the apparatus (1) of FIG. 1.

It has bypass (711) around the pump (17), as a protection of the pump against any blockage in the system.

It is activated automatically by appropriate means, e.g. it is normally blocked by a bursting disc (not shown), or a pressure-activated motorised valve.

Figure 9:
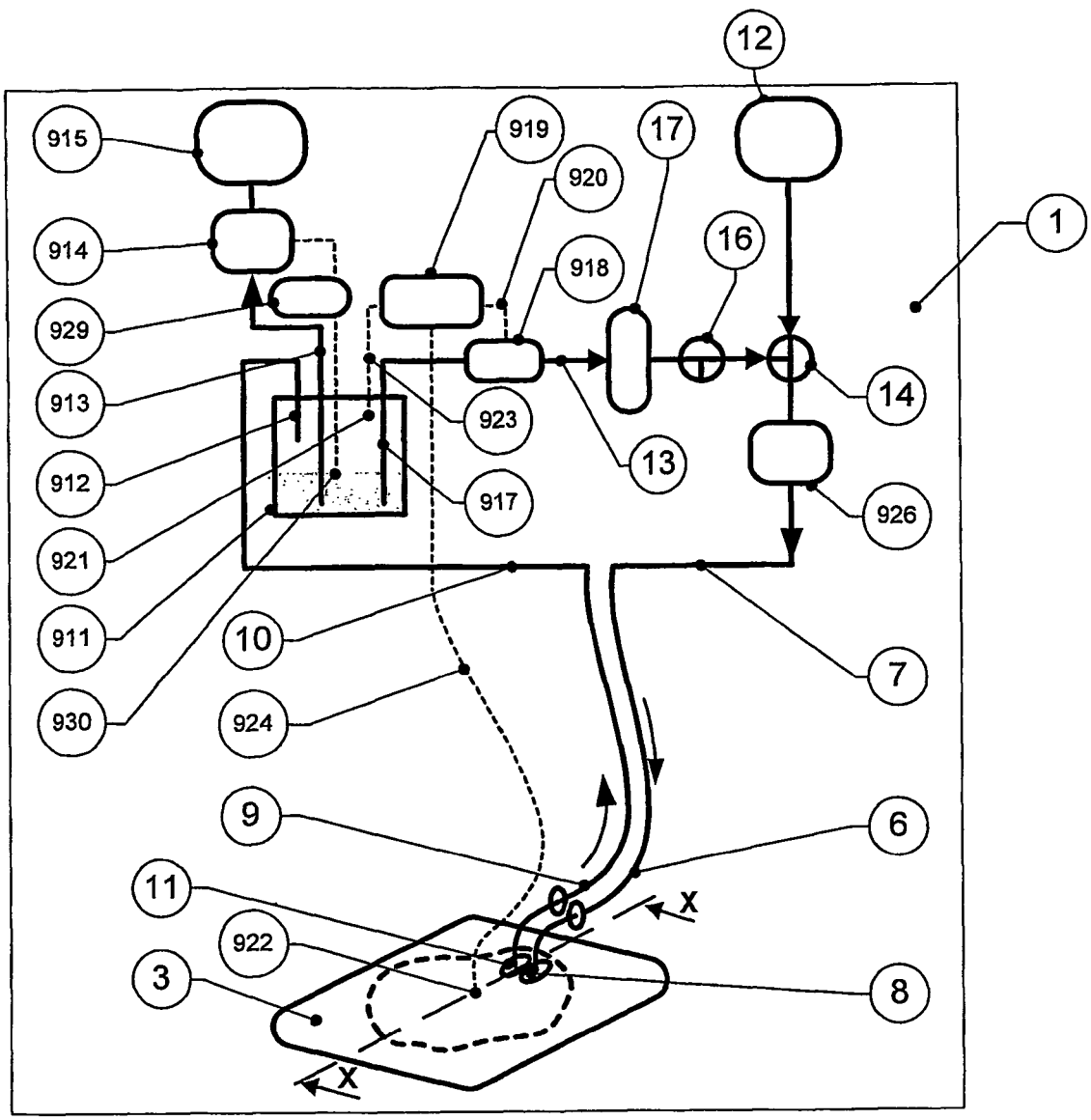
FIG. 9 is a schematic view of another apparatus for aspirating, irrigating and/or cleansing a wound according to the first aspect of the present invention. It has a single-phase system means for fluid cleansing in the form of an ultrafiltration unit.

An alternative to the by-pass (711) is a pressure sensor for the monitoring of pressure in the system and a control feedback circuit for its regulation, e.g. a pressure sensor at a point in the wound space for the monitoring of negative pressure there, which communicates with a control feedback circuit that will shut down the pump when the sensor detects excessive negative pressure. Such a pressure sensor for the monitoring of pressure in the system and a control feedback circuit for its regulation is depicted in FIG. 9.

Another alternative to the by-pass (711) is a pressure sensor mounted downstream of the pump for the monitoring of positive pressure there, which communicates with a control feedback circuit that will shut down the pump when the sensor detects excessive positive pressure from resistance, e.g. in the means for fluid cleansing that is likely to cause the system to fail catastrophically (e.g. burst tubes).

Figure 8:
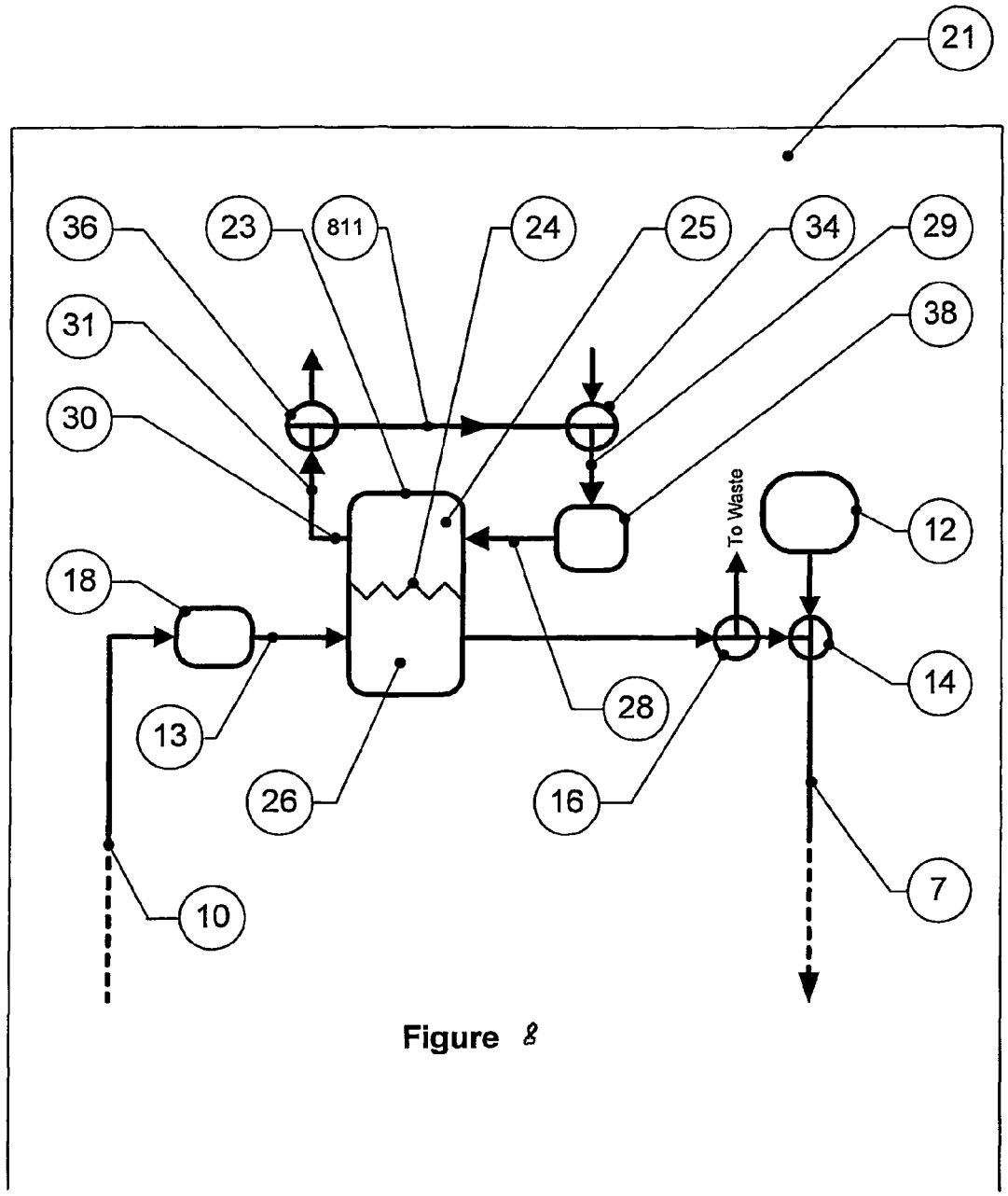
FIG. 8 is a schematic view of an apparatus for aspirating, irrigating and/or cleansing a wound according to the first aspect of the present invention. It has a two-phase system means for fluid cleansing in the form of a dialysis unit, or a biphasic extraction unit.

Referring to FIG. 8, the apparatus (1) for aspirating, irrigating and/or cleansing wounds is a variant of the apparatus (1) of FIG. 2.

The latter is a two-phase system with a dialysis unit (21), but is one in which dialytic fluid passes only once across the surface of the dialytic membrane (28) in the first chamber (25) from a dialysate reservoir (not shown) to waste via a second bleed T-valve (36) into, e.g. a collection bag (not shown).

This variant has a dialysate recirculation tube (811) running between a first T-valve (816) on the inlet side of the dialysate pump (23) and a second T-valve (817) to permit the pump (23) to recirculate the dialysate once the circuit is primed in multiple passes through the dialysis unit (21).

The operation of the system will be apparent to the skilled person.

Referring to FIG. 9, the apparatus (1) for aspirating, irrigating and/or cleansing wounds is a major variant of the apparatus shown in FIG. 1.

The device for moving fluid through the wound and means for fluid cleansing (17) in FIG. 1 is a peristaltic pump (18), e.g. preferably a small portable peristaltic pump, acting on the fluid circulation tube (13) downstream of the dressing (2) to apply an overall low negative pressure in the wound space.

In the apparatus (1) shown in FIG. 9, the peristaltic pump (18) is replaced by:
a) a peristaltic pump (926) acting on the fluid supply tube (7) upstream of the dressing (2), and
b) a vacuum pump assembly (918) with pressure regulating means, acting on the fluid circulation tube (13) downstream of the dressing (2),
to apply an overall low negative pressure in the wound space.

The vacuum pump assembly comprises a tank (911) with
an inlet tube (912) connecting to the fluid circulation tube (13) and communicating with the upper part of the tank (911),
a waste tube (913) connecting to a waste pump (914) with waste bag (915) and communicating with the lower part of the tank (911),
a pump tube (917) connecting to a vacuum pump (918) and communicating with the upper part of the tank (911), and connecting via the fluid circulation tube (13) to the means for cleansing (17) and communicating with the lower part of the tank (911).

The vacuum pump (918) is controlled by a pressure feedback regulator (919) through an electrical line (920), the regulator receiving signals from a tank sensor (921) in the upper part of the tank (911), and a dressing sensor (922) in the wound space respectively via lines (923) and (924).

The waste pump (914) is controlled by a waste level feedback regulator (929) the regulator receiving signals from a tank sensor with electrical line (930) in the middle part of the tank (911).

The vacuum pump (918) either acts as a valve so that the pump tube 917 connecting to the vacuum pump (918) is normally blocked to prevent passage of air through it from the upper part of the tank (911) when the vacuum pump (918) is at rest, or the pump tube (917) is provided with a manual or motorised, e.g. pressure-activated motorised, valve (930) (not shown), so that the pump tube (917) connecting to the vacuum pump (918) may be blocked to prevent such passage.

The operation of the apparatus (1) is similar to that of the apparatus in FIG. 1 mutatis mutandis.

In use of the apparatus (1), the valve (16) is opened to a collection bag (not shown), and the T-valve (14) is turned to admit fluid from the fluid reservoir to the wound dressing through the fluid supply tube (7) and inlet pipe (6).

The pump (926) is started to nip the fluid recirculation tube (7) with the peripheral rollers on its rotor (not shown) to apply a low positive pressure on the wound.

The vacuum pump (918) either acts as a valve since it is at rest, or the valve (930) (not shown) is closed, so that the pump tube (917) is blocked to prevent passage of air through it from the upper part of the tank (911).

Irrigant pumped from the wound dressing (2) through the fluid offtake tube (10) is pumped through the lower part of the tank (911) up the outlet tube (917) via the means for cleansing (17) to the bleed T-valve (16) into, e.g. a collection bag (not shown).

The peristaltic pump (926) acting on the fluid supply tube (7) upstream of the dressing (2) is allowed to run until the apparatus is primed throughout the whole length of the apparatus flow path and excess fluid is voided to waste via the bleed T-valve (16) into the collection bag.

The T-valve (14) is then turned to switch from supply to recirculation, i.e. is set to close the wound to the fluid reservoir (12) but to admit fluid into the wound from the fluid recirculation tube (13), and the bleed T-valve (16) is simultaneously closed.

The vacuum pump (918) is then activated, and, if the vacuum pump (918) does not act as a valve when at rest, the valve (930) in the pump tube (917) is opened, to apply a low negative pressure to the wound.

The circulating fluid from the wound and the fluid reservoir (12) passes through the cleansing unit (17). Materials deleterious to wound healing are removed and the cleansed fluid, still containing materials that are beneficial in promoting wound healing, is returned via the recirculation tube (13) to the wound bed.

The pressure feedback regulator (919) regulates the pressure at the wound and/or the tank (911).

If the amount of fluid in circulation becomes excessive, e.g. because the wound continues to exude heavily, the waste pump (914) may be started by the waste level feedback regulator (929) on the regulator receiving signals from the tank sensor with electrical line (930).

The recirculation of fluid may be continued as long as desired.

The vacuum pump (918) is then deactivated, and, if the vacuum pump (918) does not act as a valve when at rest, the valve (930) in the pump tube (917) is closed, and the bleed T-valve (16) is opened to air to relieve the low negative pressure in the tank (911) via the means for cleansing (17) and the outlet tube (917).

Switching between supply and recirculation is then reversed, by turning the T-valve (14) to admit fluid from the fluid reservoir to the wound dressing through the fluid supply tube (7) and inlet pipe (6).

The bleed valve (16) is left open, so that fresh fluid flushes the recirculating system. The running of the pump (918) may be continued until the apparatus is flushed, when it and the fluid recirculation is stopped.

The use of the apparatus of the present invention will now be described by way of example only in the following Example:

EXAMPLE 1

The Combination of the Removal by Dialysis of Materials Deleterious to Wound Healing ($H_2O_2$) by an Enzyme (Catalase) Retained in a Moving Second Phase and the Transmission of Heat to a Moving First Phase An apparatus of the present invention was constructed essentially as in FIG. 2, i.e. one in which the means for fluid cleansing is a two-phase system dialysis unit. In such an apparatus, an irrigant and/or wound exudate first phase from the wound recirculates through a first circuit and passes in through the dialysis unit in contact across a selectively permeable dialysis membrane with a second fluid (dialysate) phase. The dialysis unit was operated with the two phases flowing counter-current to each other.

Hydrogen peroxide is produced in conditions of oxidative stress following reduced blood flow and or the inflammatory response to bacterial contamination of wounds. It may be removed by the appropriate antagonists and/or degraders, which include enzymic or other inhibitors, such as peroxide degraders, e.g. catalase.

The first circuit comprised a surrogate wound chamber (Minucells perfusion chamber) in which normal diploid human fibroblasts were cultured on 13 mm diameter (Thermanox polymer) cover slips retained in a two-part support (Minnucells Minusheets). Tissues present in the healing wound that must survive and proliferate were represented by the cells within the chamber. Nutrient medium (DMEM with 10% FCS with 1% Buffer All) to simulate wound exudate was pumped from a reservoir into the lower aspect of the chamber where it bathed the fibroblasts and was removed from the upper aspect of the chamber and returned to the reservoir.

The first circuit also comprised a) Upstream of the wound chamber, a luer-fitting hollow fibre tangential membrane dialysis unit (Spectrum® MicroKros® X14S-100-04N, 8 cm² surface area, 400 KD Mol. Wt. cut off,) through which a second cleansing circuit containing nutrient media with between 5,000 and 50,000 units (µ moles $H_2O_2$ degraded per min at pH7, 25° C.) per ml of catalase (in a circuit with a reservoir and total volume of between 5.0 mL and 20 mL) at a flow rate of between 0.5 ml min$^{-1}$ and 5.0 ml min$^{-1}$ could be passed in a counter current direction, and b) upstream of the wound chamber, a heat exchanger such that the temperature of the nutrient media bathing the cells reaches between 35° C. and 37° C.

The pumps for the two circuits were peristaltic pumps acting on silicone tubing or equivalent. The internal diameter of the tubing was 1.0 mm. A total volume for the first circuit including the chamber and the reservoir at a number of values between 25 and 75 ml was used. The flow rates used were at a number of values between 0.5 ml min$^{-1}$ and 5.0 ml min$^{-1}$.

Experiments were conducted that simulated conditions not uncommon for healing wounds whereby the chamber simulating the wound was placed in a room temperature environment (simulating the low temperatures often experienced in wounds where blood flow is poor) and the nutrient medium containing a material deleterious to wound healing, namely hydrogen peroxide, was circulated over the cells.

First and second control apparatus were also constructed essentially as in FIG. 2, but where either a) the cleansing membrane dialysis unit is omitted, so that the nutrient flow passes directly from the reservoir, or
b) the heat exchanger is omitted, so that the nutrient flow bathing the cells does not reach between 35° C. and 37° C. and remains at between 18° C. and 20° C.

In controls where either a) the passage of the nutrient flow through the cleansing membrane dialysis unit or
b) the heat exchanger unit is omitted, and the concentration of $H_2O_2$ lies between 5 and 20 mM and the temperature of the nutrient medium bathing the cells is between 18° C. and 20° C., survival and growth of the fibroblasts is inhibited.

However, when the nutrient medium flow in the first circuit is c) connected into the ends of the membrane dialysis unit through which a second cleansing circuit containing catalase (at the concentrations and flow rates noted above) is passing in a counter current direction, and
d) passes through a heat exchanger so that the temperature of the nutrient media bathing the cells reaches between 35° C. and 37° C., the fibroblasts survive and proliferate to a greater extent during a 24 hour period than the control circuits.

EXAMPLE 2

The Combination of the Removal by Dialysis of Materials Deleterious to Wound Healing ($H_2O_2$) by an Enzyme (Catalase) Retained in a Static Second Phase and the Transmission of Heat to a Moving First Phase An apparatus of the present invention was constructed essentially as in FIG. 2, i.e. one in which the means for fluid cleansing is a two-phase system dialysis unit. In such an apparatus, an irrigant and/or wound exudate first phase from the wound recirculates through a first circuit and passes over the dialysis unit in contact across a selectively permeable dialysis membrane with a second static fluid (dialysate) phase.

Hydrogen peroxide is produced in conditions of oxidative stress following reduced blood flow and or the inflammatory response to bacterial contamination of wounds. It may be removed by the appropriate antagonists and/or degraders, which include enzymic or other inhibitors, such as peroxide degraders, e.g. catalase.

The first circuit comprised a surrogate wound chamber (Minucells perfusion chamber) in which normal diploid human fibroblasts were cultured on 13 mm diameter (Thermanox polymer) cover slips retained in a two-part support (Minnucells Minusheets). Tissues present in the healing wound that must survive and proliferate were represented by the cells within the chamber.

Nutrient medium (DMEM with 10% FCS with 1% Buffer All) to simulate wound exudate was pumped from a reservoir into the lower aspect of the chamber where it bathed the fibroblasts and was removed from the upper aspect of the chamber and returned to the reservoir.

The first circuit also comprised a) for the static second phase, a length of dialysis tubing (Pierce Snake skin 68100 CG 49358B, 10 KD cut off) placed within the first circuit reservoir in which a second static cleansing circuit containing nutrient media with between 5,000 and 50,000 units (μ moles $H_2O_2$ degraded per min at pH7, 25° C.) per ml of catalase (in a circuit with a reservoir and total volume of between 5.0 ml and 20 ml)
b) upstream of the wound chamber, a heat exchanger such that the temperature of the nutrient media bathing the cells reaches between 35° C. and 37° C.

The pumps for the circuit were peristaltic acting on silicone elastic tubing or equivalent. The internal diameter of the tubing was 1.0 mm. A total volume for the first circuit including the chamber and the reservoir at a number of values between 25 and 75 ml was used. The flow rates used were at a number of values between 0.5 ml min$^{-1}$ and 5.0 ml min$^{-1}$.

Experiments were conducted that simulated conditions not uncommon for healing wounds whereby the chamber simulating the wound was placed in a room temperature environment (simulating the low temperatures often experienced in wounds where blood flow is poor) and the nutrient medium containing a material deleterious to wound healing, namely hydrogen peroxide, was circulated over the cells.

First and second control apparatus were also constructed essentially as in FIG. 2, but where either e) the cleansing membrane dialysis unit is omitted, so that the nutrient flow passes directly from the reservoir, or
f) the heat exchanger is omitted, so that the nutrient flow bathing the cells does not reach between 35° C. and 37° C. and remains at between 18° C. and 20° C.

In controls where either a) the passage of the nutrient flow past or through the cleansing membrane dialysis unit or
b) the heat exchanger unit is omitted, and the concentration of $H_2O_2$ lies between 5 and 20 mM and the temperature of the nutrient medium bathing the cells is between 18° C. and 20° C., survival and growth of the fibroblasts is inhibited.

However, when the nutrient medium flow in the first circuit is c) passed over the membrane dialysis unit in which a second cleansing circuit containing catalase (at the concentrations and flow rates noted above) is present, and
d) passes through a heat exchanger so that the temperature of the nutrient media bathing the cells reaches between 35° C. and 37° C., the fibroblasts survive and proliferate to a greater extent during than the control circuits.

The following results were obtained: A first phase of nutrient medium containing 10 μM $H_2O_2$ at a flow rate of 1.0 ml min$^{-1}$ with a 15 ml static second phase containing 7,600 units ml$^{-1}$ catalase contained within a length of dialysis tubing placed within the first circuit reservoir. The effect of the catalase cleansing unit and the heat exchanger was as follows:

| Conditions | Mean level of cell activity after 43 hrs* (n = 6) |
|---|---|
| $H_2O_2$ in media at 18° C. | 0.0 |
| $H_2O_2$ in media with catalase second phase dialysis unit at 18° C. | 0.27 |

-continued

| Conditions | Mean level of cell activity after 43 hrs* (n = 6) |
| --- | --- |
| Normal medium control at 18° C. | 0.40 |
| $H_2O_2$ in media at 37° C. | 0.0 |
| $H_2O_2$ in media with catalase at 37° C. second phase dialysis unit | 0.76 |
| Normal medium control at 37° C. | 0.55 |

*Cell activity measured with WST (Tetrazolium based mitochondrial dehdrogenase activity assay)

CONCLUSIONS

The combination of the cleansing dialysis unit that removes and degrades $H_2O_2$ and the heat exchanger unit that maintains the wound chamber between 35° C. and 37° C. enhances the cell response necessary for wound healing.

The invention claimed is:

1. An apparatus for irrigating, supplying thermal energy to, and cleansing wounds, comprising:
a fluid flow path, comprising:
    a conformable wound dressing, comprising a backing layer which is capable of forming a relatively fluid-tight seal or closure over a wound and a wound-facing face, at least one inlet pipe passing through and/or under the wound-facing face and directly or indirectly communicating with at least a fluid reservoir, and at least one outlet pipe passing through and/or under the wound-facing face, wherein a relatively fluid-tight seal or closure is formed over the wound at the point at which each inlet pipe and each outlet pipe passes through and/or under the wound-facing face;
    a means for fluid cleansing in direct or indirect communication at least with the outlet pipe;
and
    a fluid recirculation tube for directing cleansed fluid from the means for fluid cleansing back into the inlet pipe without passing through the reservoir so that at least nutrients, molecules, factors, physiologically active components and/or other components from the wound dressing that aid in proliferation or that are favorable to the wound healing process are returned to the wound;
a device for moving fluid through at least the wound dressing and the means for fluid cleansing;
a means for supplying thermal energy to at least the recirculated fluid provided to the wound so as to maintain the wound at a temperature between 34 and 40 degrees Celsius to optimize the metabolic activities of physiologically active components within the wound dressing and promote wound healing, and
a means for bleeding the fluid flow path to bleed fluid from the recirculation tube to relieve pressure within the fluid flow path.

2. An apparatus according to claim 1, wherein the means for supplying thermal energy to the fluid provided to the wound comprises a heater and/or a conductively heated component of the apparatus flow path.

3. An apparatus according to claim 1, wherein the means for supplying thermal energy to the fluid provided to the wound comprises a radiative heater.

4. An apparatus according to claim 1, wherein the means for supplying thermal energy to the fluid provided to the wound comprises a conductively heated component of the apparatus flow path and a radiative heater.

5. An apparatus according to claim 1, wherein the means for fluid cleansing is a single-phase system, in which circulating fluid from the wound passes through the means for fluid cleansing and materials deleterious to wound healing are removed without the circulating fluid coming into direct or indirect contact with another fluid in the means for fluid cleansing.

6. An apparatus according to claim 1, wherein the means for fluid cleansing is a two-phase system, in which circulating fluid from the wound passes through the means for fluid cleansing and materials deleterious to wound healing are removed by the circulating fluid coming into direct or indirect contact with another fluid in the means for fluid cleansing.

7. An apparatus according to claim 6, wherein the circulating fluid from the wound and the other fluid in the means for fluid cleansing are separated by an integer which is selectively permeable to materials deleterious to wound healing.

8. An apparatus according to claim 6, wherein the circulating fluid from the wound and the other fluid in the means for fluid cleansing are separated by an integer which is not selectively permeable to materials deleterious to wound healing, and the other fluid comprises and/or is in contact with a material that removes materials deleterious to wound healing.

9. A method of treating wounds to promote wound healing using the apparatus for aspirating, irrigating and/or cleansing wounds according to claim 1.

10. An apparatus according to claim 1, wherein the means for supplying thermal energy comprises a heater configured to supply thermal energy to fluid in the at least one inlet pipe.

11. An apparatus according to claim 1, wherein the apparatus is configured such that at least a portion of fluid flowing through the outlet pipe is directed to a waste reservoir.

12. A method of treating a wound, comprising:
providing a conformable wound dressing having a cover configured to form a relatively fluid-tight seal around at least a portion of a wound;
providing an apparatus for irrigating and/or cleansing a wound comprising:
    at least one inlet pipe configured to communicate with the cover and configured to provide a fluid conduit between at least a fluid reservoir and the cover so that fluid can flow into the cover; and
    at least one outlet pipe configured to communicate with the cover and configured to provide a fluid conduit so that fluid can flow out of the cover, wherein the fluid in the cover comprises physiologically active components;
pumping fluid through at least the inlet pipe, the cover, and the outlet pipe;
cleansing the fluid that flows out of the cover;
regulating the fluid that flows out of the cover so that a portion of the fluid that flows out of the cover comprising physiologically active components is recirculated back to the cover without passing through the reservoir after being cleansed and a portion of the fluid that flows out of the cover is bled through a bleed mechanism and is provided to a waste reservoir to relieve pressure within the cover; and
heating the fluid before the fluid enters the cover to maintain the wound at an approximately normothermic range to optimize the metabolic activities of the physiologically active components within the cover and promote wound healing.

13. The method of claim 12, wherein the normothermic range is from approximately 34 and 40 degrees Celsius.

14. The method of claim 12, further comprising adjusting the proportion of the amount of fluid that is provided to the cover after being cleansed and the amount of fluid provided to the cover from the fluid reservoir.

15. An apparatus for irrigating, supplying thermal energy to, and cleansing wounds, comprising:

a wound dressing comprising a backing layer configured to form a relatively fluid-tight seal around at least a portion of a wound;

at least one inlet pipe configured to communicate with the backing layer and to provide a fluid conduit into the backing layer;

at least one outlet pipe configured to communicate with the backing layer and to provide a fluid conduit out of the backing layer;

a fluid reservoir comprising irrigation fluid in fluid communication with the inlet pipe to supply irrigation fluid from the fluid reservoir into the backing layer;

a fluid pump configured to pump fluid through at least the inlet pipe, the backing layer, and the outlet pipe;

a fluid cleansing mechanism in fluid communication with the outlet pipe;

a recirculation tube in fluid communication with the fluid cleansing mechanism configured to recirculate fluid cleansed by the fluid cleansing mechanism back into the inlet pipe without passing through the fluid reservoir, the fluid recirculation tube having a bleed valve to bleed fluid from the recirculation tube to relieve pressure within at least a portion of the apparatus, the recirculated fluid comprising physiologically active components; and a heat source configured to heat at least the recirculated fluid before the fluid enters the backing layer, the heat source configured so that the fluid maintains the wound at an approximately normothermic range to optimize the metabolic activities of physiologically active components within the backing layer and promote wound healing.

16. An apparatus according to claim 15, wherein the thermal energy provided to the wound maintains the wound between approximately 34 and 40 degrees Celsius.

17. An apparatus according to claim 15, wherein the heat source comprises a radiative heater.

18. An apparatus according to claim 1, wherein the means for supplying thermal energy to the fluid provided to the wound is supported by the backing layer.

19. An apparatus according to claim 1, wherein the means for supplying thermal energy to the fluid provided to the wound is configured to surround at least a portion of at least one inlet pipe.

20. The method of claim 12, comprising heating the fluid before the fluid enters the cover with a heat source supported by the cover.

21. The method of claim 12, comprising heating the fluid before the fluid enters the cover with a heat source surrounding at least a portion of the at least one inlet pipe.

22. An apparatus according to claim 15, wherein the heat source is supported by the backing layer.

23. An apparatus according to claim 15, wherein the heat source is configured to surround at least a portion of the inlet pipe.

* * * * *

UNITED STATES PATENT AND TRADEMARK OFFICE
CERTIFICATE OF CORRECTION

PATENT NO. : 7,794,450 B2  
APPLICATION NO. : 10/575875  
DATED : September 14, 2010  
INVENTOR(S) : Blott et al.

Page 1 of 1

It is certified that error appears in the above-identified patent and that said Letters Patent is hereby corrected as shown below:

Title Page, Item (75) Inventors, should read

-- (75) Inventors: Patrick Lewis Blott, Barmby Moor (GB); Bryan Greener, Elvington (GB); Edward Yerbury Hartwell, Hull (GB); Julian Lee-Webb, Copmanthorpe (GB); Derek Nicolini, Brough (GB); Clare Green, Crockey Hill (GB); Robin Paul Martin, Wheldrake (GB); Tina Michelle Walker, Shelton (GB) --.

Signed and Sealed this  
Twenty-fourth Day of November, 2015

Michelle K. Lee  
*Director of the United States Patent and Trademark Office*